United States Patent
Zheng et al.

(10) Patent No.: US 9,051,284 B2
(45) Date of Patent: *Jun. 9, 2015

(54) COMPOUNDS FOR POROUS FILMS IN LIGHT-EMITTING DEVICES

(75) Inventors: Shijun Zheng, San Diego, CA (US); Jensen Cayas, Bonita, CA (US); David T. Sisk, San Diego, CA (US)

(73) Assignee: NITTO DENKO CORPORATION, Osaka (JP)

( * ) Notice: Subject to any disclaimer, the term of this patent is extended or adjusted under 35 U.S.C. 154(b) by 539 days.

This patent is subject to a terminal disclaimer.

(21) Appl. No.: 13/410,778

(22) Filed: Mar. 2, 2012

(65) Prior Publication Data
US 2012/0226046 A1 Sep. 6, 2012

Related U.S. Application Data

(60) Provisional application No. 61/449,034, filed on Mar. 3, 2011.

(51) Int. Cl.
| C07D 413/14 | (2006.01) |
| C07D 413/10 | (2006.01) |
| C07D 417/14 | (2006.01) |
| C07D 263/64 | (2006.01) |
| C09K 11/06 | (2006.01) |
| H01L 51/52 | (2006.01) |

(52) U.S. Cl.
CPC ............. *C07D 263/64* (2013.01); *C09K 11/06* (2013.01); *C07D 413/14* (2013.01); *C07D 417/14* (2013.01); *H01L 51/5268* (2013.01)

(58) Field of Classification Search
CPC .. C07D 263/64; C07D 417/14; C07D 413/14; H01L 51/5268; H01L 51/50; H01L 51/54; H05B 33/14; C09K 11/06
See application file for complete search history.

(56) References Cited

U.S. PATENT DOCUMENTS

| 3,798,231 A | 3/1974 | Fleck et al. |
| 3,821,240 A | 6/1974 | Aebli et al. |
| 3,940,410 A | 2/1976 | Kittl |
| 4,892,953 A | 1/1990 | Arnold et al. |
| 5,081,256 A | 1/1992 | Arnold et al. |
| 5,998,626 A | 12/1999 | Sato |
| 6,171,715 B1 | 1/2001 | Sato et al. |

(Continued)

FOREIGN PATENT DOCUMENTS

| CN | 101 759 648 | 6/2010 |
| CN | 101 851 210 | 10/2010 |

(Continued)

OTHER PUBLICATIONS

Debeaux et al., "Charge-Transporting Polymers based on Phenylbenzoimidazole Moieties," Advanced Functional Materials, 2010, vol. 20, pp. 399-408.

(Continued)

*Primary Examiner* — Dawn Garrett
(74) *Attorney, Agent, or Firm* — Knobbe Martens Olson & Bear LLP

(57) ABSTRACT

Compounds useful in porous films for light extraction and/or light scattering in electronic devices, such as light-emitting devices, are described herein. These compounds may be represented by Formula 1, as described herein.

$Rg^5\text{-}Rg^3\text{-}Rg^1\text{-}Rg^2\text{-}Rg^4$ (Formula 1)

19 Claims, 23 Drawing Sheets

(56) References Cited

U.S. PATENT DOCUMENTS

2011/0059867 A1 3/2011 Kim et al.
2011/0196158 A1* 8/2011 Zheng .................. 546/256

FOREIGN PATENT DOCUMENTS

| JP | 45-018750 | 6/1970 |
|---|---|---|
| JP | 2001-097962 | 4/2001 |
| JP | 2003-342266 | 12/2003 |
| JP | 2005-044790 | 2/2005 |
| JP | 2008-120696 | 5/2008 |
| JP | 2008-195830 | 8/2008 |
| JP | 2008-239873 | 10/2008 |
| WO | WO 2009/009756 | 1/2009 |
| WO | WO 2011/021689 | 2/2011 |
| WO | WO 2011/097260 | 8/2011 |
| WO | WO 2012/119099 | 9/2012 |

OTHER PUBLICATIONS

Haga et al., "Molecular Design of a Proton-Induced Molecular Switch Based on Rod-Shaped Ru Dinuclear Complexes with Bis-Tridentate 2,6-bis(benzimidazol-2-yl)pyridine Derivatives," Dalton Transactions, 2003, pp. 2069-2079.

Kim et al., "Highly Emissive Self-assembled Organic Nanoparticles having Dual Color Capacity for Target Immunofluorescence Labeling," Advanced Materials, 2008, vol. 20, pp. 1117-1121.

Luo et al., "A New Blue Light-Emitting Terphenyl-Bridged Bisbenzimidazolium Salts: Synthesis, Crystal Structure, and Photophysical Properties," Dyes and Pigments, 2011, vol. 92, pp. 596-602.

International Search Report and the Written Opinion in PCT Application No. PCT/US2012/027535, dated May 31, 2012.

International Preliminary Report on Patentability in PCT Application No. PCT/US2012/027535, dated Sep. 3, 2013.

* cited by examiner

COMPOUNDS FOR POROUS FILMS IN LIGHT-EMITTING DEVICES

CROSS-REFERENCE TO RELATED APPLICATIONS

The present application claims priority under 35 U.S.C. §119(e) to U.S. Provisional Application No. 61/449,034 filed on Mar. 3, 2011, the disclosures of which is incorporated by reference herein in its entirety.

BACKGROUND OF THE INVENTION

1. Field

Some embodiments relate to compounds for use in porous films, such as porous films for use in devices, such as light-emitting devices.

2. Description of the Related Art

Organic light-emitting devices (OLED) may be useful for incorporating into energy-efficient lighting equipment or devices. Unfortunately, the efficiency of OLEDs may be limited by both any inherent inefficiency in producing emitted light, and in the ability of emitted light to escape the device to provide lighting. The inability of emitted light to escape the device may also be referred to as trapping. Because of trapping, the efficiency of a device may be reduced to about 10-30% of the emissive efficiency. Light extraction may reduce trapping and thus substantially improve efficiency.

SUMMARY

Porous films may be useful in devices such as OLEDs for light extraction and/or light scattering. A porous film may comprise a non-polymeric organic compound. Some embodiments include a compound represented by Formula 1:

$$Rg^5\text{-}Rg^3\text{-}Rg^1\text{-}Rg^2\text{-}Rg^4 \qquad \text{(Formula 1)}$$

wherein $Rg^1$, $Rg^3$, and $Rg^2$ are independently optionally substituted pyridinyl or phenyl; and $Rg^5$ and $Rg^4$ are independently optionally substituted benzimidazol-2-yl, benzooxazol-2-yl, or benzothiazol-2-yl.

Some embodiments include a light emitting device comprising a compound disclosed herein.

These and other embodiments are described in greater detail herein.

Figure 1:
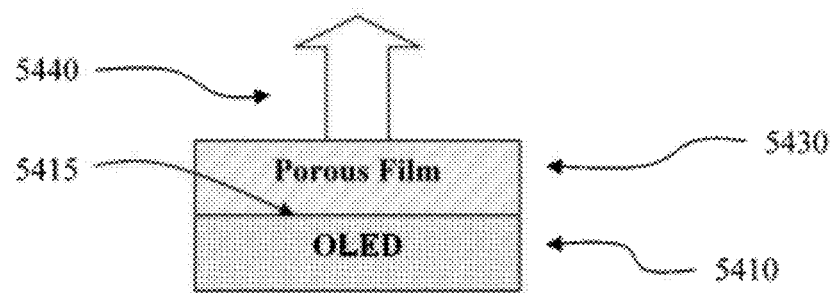
FIG. 1 is a schematic diagram of some embodiments of a device described herein.

These and other embodiments are described in detail herein.

DETAILED DESCRIPTION

Unless otherwise indicated, when a chemical structural feature such as phenyl or pyridinyl is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent may be an ordinary organic moiety known in the art, which may have a molecular weight (e.g. the sum of the atomic masses of the atoms of the substituent) of less than about 500 g/mol, about 300 g/mol, about 200 g/mol, about 100 g/mol, or about 50 g/mol. In some embodiments, the substituent comprises: 0-30, 0-20, 0-10, or 0-5 carbon atoms; and 0-30, 0-20, 0-10, or 0-5 heteroatoms independently selected from: N, O, S, Si, F, Cl, Br, or I; provided that the substituent comprises at least one atom selected from: C, N, O, S, Si, F, Cl, Br, or I. Examples of substituents include, but are not limited to, alkyl, alkenyl, alkynyl, heteroalkyl, heteroalkenyl, heteroalkynyl, aryl, heteroaryl, arylalkyl, heteroarylalkyl, arylheteroalkyl, heteroarylheteroalkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof.

As used herein the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl (—CH$_3$), ethyl (—CH$_2$CH$_3$), n-propyl (—CH$_2$CH$_2$CH$_3$), n-butyl (—CH$_2$CH$_2$CH$_2$CH$_3$), n-pentyl (—CH$_2$CH$_2$CH$_2$CH$_2$CH$_3$), n-hexyl (—CH$_2$CH$_2$CH$_2$CH$_2$CH$_2$CH$_3$), etc.; $C_{3-10}$ branched alkyl, such as $C_3H_7$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

The structures of some of the moieties referred to herein are depicted below. These moieties may be unsubstituted, as shown below, or a substituent may independently be in any position normally occupied by a hydrogen atom when the moiety is unsubstituted.

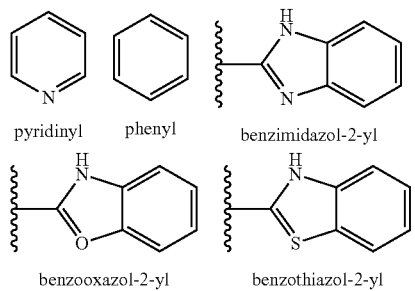

pyridinyl  phenyl  benzimidazol-2-yl benzooxazol-2-yl  benzothiazol-2-yl

Some embodiments include a compound represented by one or more of Formulas 2-19.

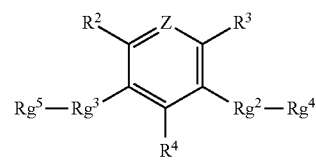

Formula 2

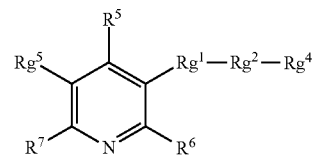

Formula 3

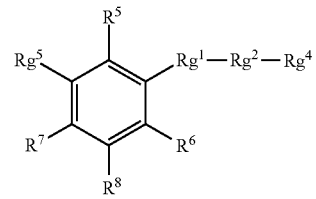

Formula 4

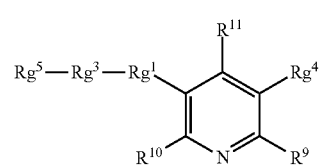

Formula 5

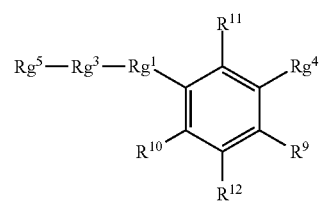

Formula 6

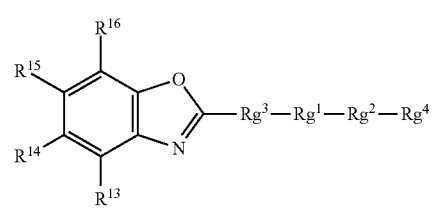

Formula 7

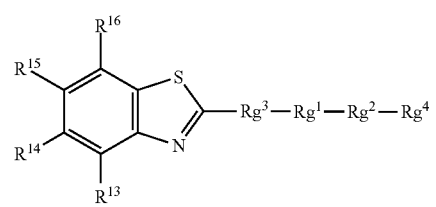

Formula 8

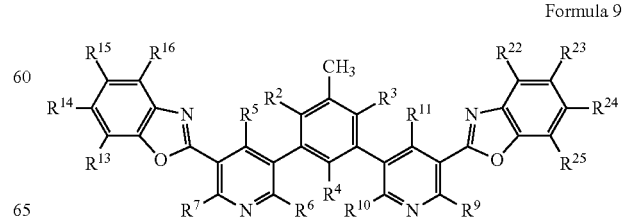

Formula 9

-continued

Formula 10
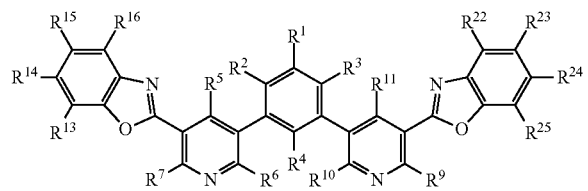

Formula 11
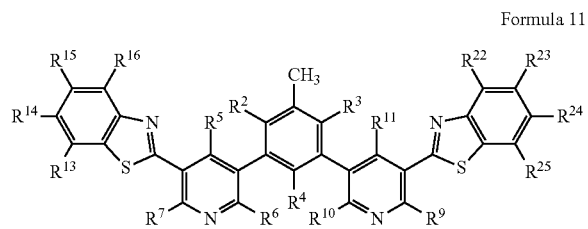

Formula 14
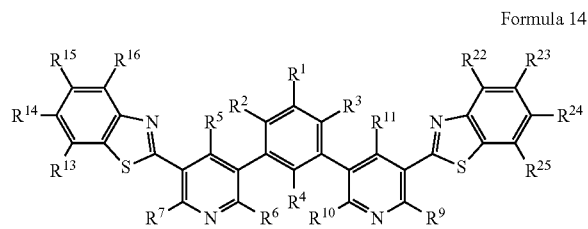

Formula 15
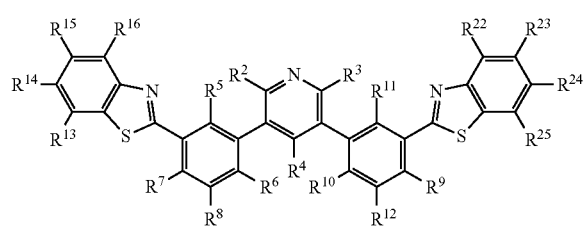

Formula 16
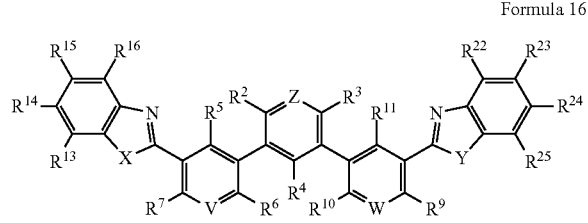

Formula 17
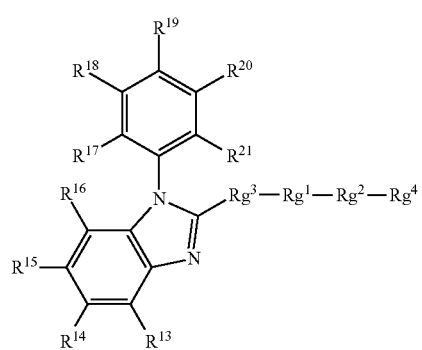

-continued

Formual 18
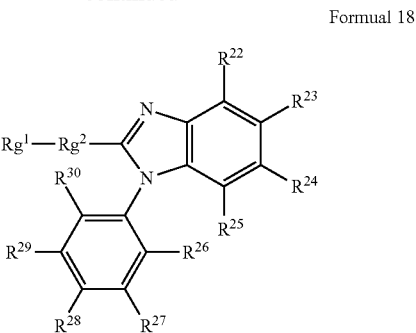

With respect to any relevant formula above, $Rg^1$ may be optionally substituted pyridinyl or phenyl. $Rg^1$ may include any substituent, such as those described herein. In some embodiments, $Rg^1$ may independently be F, Cl, CN, $C_{1-6}$ alkyl, —O—$C_{1-6}$ alkyl, OH, or $CF_3$. In some embodiments, any substituent of $Rg^1$ may independently be H; $C_{1-6}$ alkyl, such as methyl, ethyl, propyl isomers (e.g. n-propyl, isopropyl, etc.), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, etc.; or —O—$C_{1-6}$ alkyl, such as —O-methyl (e.g. —$OCH_3$), —O-ethyl (e.g. —$OCH_2CH_3$), isomers of —O-propyl (e.g. —$OCH_2CH_2CH_3$—, —$OCH(CH_3)_2$, etc.), —O-cyclopropyl, isomers of —O-butyl, isomers of —O-cyclobutyl (e.g. —O-cyclobutyl, —O-methylcyclopropyl, etc.), isomers of —O-pentyl, isomers of —O-cyclopentyl, isomers of —O-hexyl, isomers of —O-cyclohexyl, etc. In some embodiments, $Rg^1$ is unsubstituted.

In some embodiments, $Rg^1$ in any relevant formula above may be:

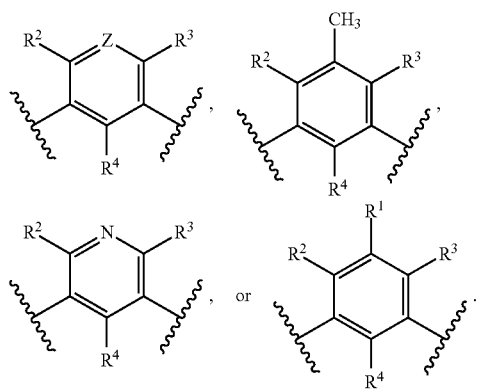

With respect to any relevant formula above, $Rg^2$ may be optionally substituted pyridinyl or phenyl. $Rg^2$ may include any substituent, such as those described herein. In some embodiments, any substituent of $Rg^2$ may independently be F, Cl, CN, $C_{1-6}$ alkyl, —O—$C_{1-6}$ alkyl, OH, or $CF_3$. In some embodiments, any substituent of $Rg^2$ may independently be H; $C_{1-6}$ alkyl, such as methyl, ethyl, propyl isomers (e.g. n-propyl, isopropyl, etc.), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, etc.; or —O—$C_{1-6}$ alkyl, such as —O-methyl, —O-ethyl, isomers of —O-propyl (e.g. —O-n-propyl, —O-isopropyl, etc.), —O-cyclopropyl, isomers of —O-butyl, isomers of —O-cyclobutyl (e.g. —O-cyclobutyl, —O-methylcyclopropyl, etc.), isomers of —O-pentyl, isomers of —O-cyclopentyl, isomers of —O-hexyl, isomers of —O-cyclohexyl, etc. In some embodiments, $Rg^2$ is unsubstituted.

In some embodiments, $Rg^2$ in any relevant formula above may be:

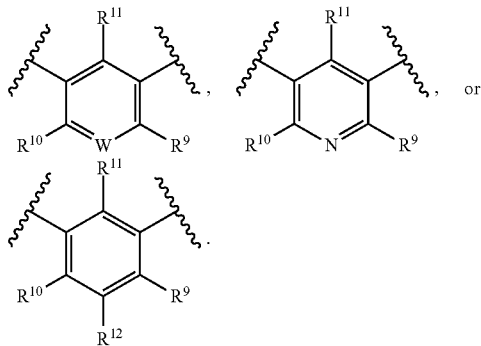

With respect to any relevant formula above, $Rg^3$ may be optionally substituted pyridinyl or phenyl. $Rg^3$ may include any substituent, such as those described herein. In some embodiments, any substituent of $Rg^3$ may independently be F, Cl, CN, $C_{1-6}$ alkyl, —O—$C_{1-6}$ alkyl, OH, or $CF_3$. In some embodiments, any substituent of $Rg^3$ may independently be H; $C_{1-6}$ alkyl, such as methyl, ethyl, propyl isomers (e.g. n-propyl, isopropyl, etc.), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, etc.; or —O—$C_{1-6}$ alkyl, such as —O-methyl, —O-ethyl, isomers of —O-propyl (e.g. —O-n-propyl, —O-isopropyl, etc.), —O-cyclopropyl, isomers of —O-butyl, isomers of —O-cyclobutyl (e.g. —O-cyclobutyl, —O-methylcyclopropyl, etc.), isomers of —O-pentyl, isomers of —O-cyclopentyl, isomers of —O-hexyl, isomers of —O-cyclohexyl, etc. In some embodiments, $Rg^3$ is unsubstituted.

In some embodiments, $Rg^3$ in any relevant formula above may be:

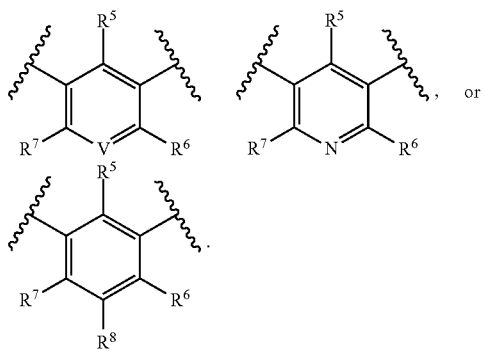

With respect to any relevant formula above, $Rg^4$ may be optionally substituted benzimidazol-2-yl, benzooxazol-2-yl, or benzothiazol-2-yl. $Rg^4$ may include any substituent, such as those described herein. In some embodiments, any substituent of $Rg^4$ may independently be F, Cl, CN, $C_{1-6}$ alkyl, —O—$C_{1-6}$ alkyl, OH, or $CF_3$. In some embodiments, any substituent of $Rg^3$ may independently be H; $C_{1-6}$ alkyl, such as methyl, ethyl, propyl isomers (e.g. n-propyl, isopropyl, etc.), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, etc.; or —O—$C_{1-6}$ alkyl, such as —O-methyl, —O-ethyl, isomers of —O-propyl (e.g. —O-n-propyl, —O-isopropyl, etc.), —O-cyclopropyl, isomers of —O-butyl, isomers of —O-cyclobutyl (e.g. —O-cyclobutyl, —O-methylcyclopropyl, etc.), isomers of —O-pentyl, isomers of —O-cyclopentyl, isomers of —O-hexyl, isomers of —O-cyclohexyl, etc. In some embodiments, $Rg^4$ is unsubstituted.

In some embodiments, $Rg^4$ in any relevant formula above may be:

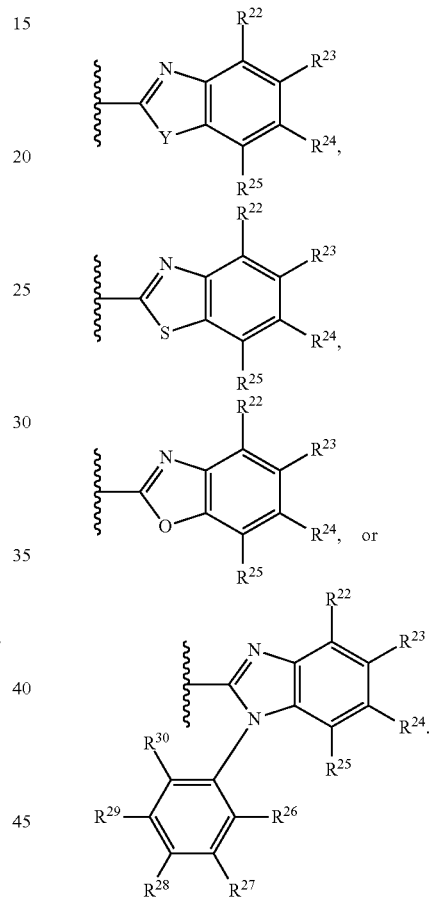

With respect to any relevant formula above, $Rg^5$ may be optionally substituted benzimidazol-2-yl, benzooxazol-2-yl, or benzothiazol-2-yl. $Rg^5$ may include any substituent, such as those described herein. In some embodiments, any substituent of $Rg^5$ may independently be F, Cl, CN, $C_{1-6}$ alkyl, —O—$C_{1-6}$ alkyl, OH, or $CF_3$. In some embodiments, any substituent of $Rg^5$ may independently be H; $C_{1-6}$ alkyl, such as methyl, ethyl, propyl isomers (e.g. n-propyl, isopropyl, etc.), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, etc.; or alkyl, such as —O-methyl, —O-ethyl, isomers of —O-propyl (e.g. —O-n-propyl, —O-isopropyl, etc.), —O-cyclopropyl, isomers of —O-butyl, isomers of —O-cyclobutyl (e.g. —O-cyclobutyl, —O-methylcyclopropyl, etc.), isomers of —O-pentyl, isomers of —O-cyclopentyl, isomers of —O-hexyl, isomers of —O-cyclohexyl, etc. In some embodiments, $Rg^3$ is unsubstituted.

In some embodiments, $Rg^5$ in any relevant formula above may be:

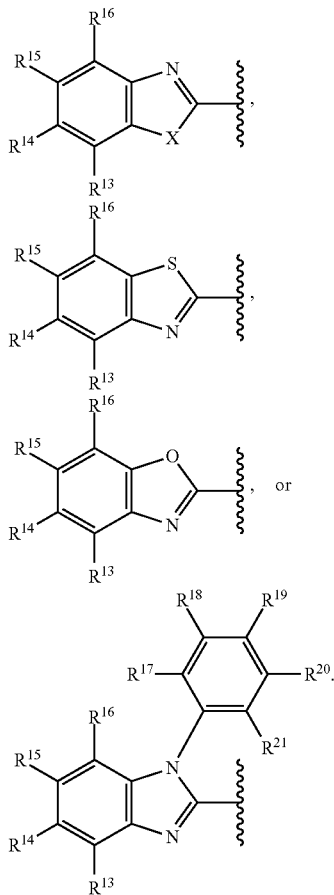

With respect to any relevant formula or structural depiction above, Z may be N or $CR^1$.

With respect to any relevant formula or structural depiction above, V may be N or $CR^8$.

With respect to any relevant formula or structural depiction above, W may be N or $CR^{12}$.

With respect to any relevant formula or structural depiction above, X may be O, S, or N-$Ph^1$.

$Ph^1$ may be phenyl optionally substituted with 1, 2, or 3 substituents independently selected from $C_{1-6}$ alkyl and O—$C_{1-6}$ alkyl.

With respect to any relevant formula or structural depiction above, Y may be O, S, or N-$Ph^2$.

$Ph^2$ may be phenyl optionally substituted with 1, 2, or 3 substituents independently selected from $C_{1-6}$ alkyl and O—$C_{1-6}$ alkyl.

With respect to any relevant formula or structural depiction above, $R^1$ may be H or any substituent. Some non-limiting examples of $R^1$ may include $R^A$, F, Cl, CN, $OR^A$, $CF_3$, $NO_2$, $NR^AR^B$, $COR^A$, $CO_2R^A$, $OCOR^A$, or optionally substituted phenyl. In some embodiments, $R^1$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or phenyl optionally substituted with 1, 2, or 3 substituents selected from: $C_{1-6}$ alkyl and —O—$C_{1-6}$ alkyl. In some embodiments, $R^1$ may be H, methyl, ethyl, isopropyl, or phenyl optionally substituted with methyl, ethyl, or —O-methyl. In some embodiments, $R^1$ is H.

Each $R^A$ may independently be H, or $C_{1-12}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, $C_7H_{15}$, cyclic $C_7H_{13}$, $C_8H_{17}$, cyclic $C_8H_{15}$, $C_9H_{19}$, cyclic $C_9H_{17}$, $C_{10}H_{21}$, cyclic $C_{10}H_{19}$, etc.

Each $R^B$ may independently be H, or $C_{1-12}$ alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, $C_7H_{15}$, cyclic $C_7H_{13}$, $C_8H_{17}$, cyclic $C_8H_{15}$, $C_9H_{19}$, cyclic $C_9H_{17}$, $C_{10}H_{21}$, cyclic $C_{10}H_{19}$, etc.

With respect to any relevant formula or structural depiction above, $R^2$ may be H or any substituent. Some non-limiting examples of $R^2$ may include $R^A$, F, Cl, CN, $OR^A$, $CF_3$, $NO_2$, $NR^AR^B$, $COR^A$, $CO_2R^A$. $OCOR^A$, etc. In some embodiments, $R^2$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^2$ may be H.

With respect to any relevant formula or structural depiction above, $R^3$ may be H or any substituent. Some non-limiting examples of $R^3$ may include $R^A$, F, Cl, CN, $OR^A$, $CF_3$, $NO_2$, $NR^AR^B$, $COR^A$, $CO_2R^A$, $OCOR^A$, etc. In some embodiments, $R^3$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^3$ may be H.

With respect to any relevant formula or structural depiction above, $R^4$ may be H or any substituent. Some non-limiting examples of $R^4$ may include $R^A$, F, Cl, CN, $OR^A$, $CF_3$, $NO_2$, $NR^AR^B$, $COR^A$, $CO_2R^A$, $OCOR^A$, etc. In some embodiments, $R^4$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^4$ may be H.

With respect to any relevant formula or structural depiction above, in some embodiments, $R^1$, $R^2$, $R^3$, and $R^4$ may independently be H, $C_{1-6}$ alkyl, or —O—$C_{1-6}$ alkyl. In some embodiments, $R^1$, $R^2$, $R^3$, and $R^4$ may be H.

With respect to any relevant formula or structural depiction above, in some embodiments, $R^2$, $R^3$, and $R^4$ may independently be H, $C_{1-6}$ alkyl, or —O—$C_{1-6}$ alkyl. In some embodiments, $R^2$, $R^3$, and $R^4$ may be H.

With respect to any relevant formula or structural depiction above, $R^5$ may be H or any substituent. Some non-limiting examples of $R^5$ may include $R^A$, F, Cl, CN, $OR^A$, $CF_3$, $NO_2$, $NR^AR^B$, $COR^A$, $CO_2R^A$, $OCOR^A$, etc. In some embodiments, $R^5$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^5$ may be H.

With respect to any relevant formula or structural depiction above, $R^6$ may be H or any substituent. Some non-limiting examples of $R^6$ may include $R^A$, F, Cl, CN, $OR^A$, $CF_3$, $NO_2$, $NR^AR^B$, $COR^A$, $CO_2R^A$, $OCOR^A$, etc. In some embodiments, $R^6$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^6$ may be H.

With respect to any relevant formula or structural depiction above, $R^7$ may be H or any substituent. Some non-limiting examples of $R^7$ may include $R^A$, F, Cl, CN, $OR^A$, $CF_3$, $NO_2$, $NR^AR^B$, $COR^A$, $CO_2R^A$, $OCOR^A$, etc. In some embodiments, $R^7$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^7$ may be H.

With respect to any relevant formula or structural depiction above, in some embodiments, $R^5$, $R^6$, and $R^7$ may independently be H, $C_{1-6}$ alkyl, or —O—$C_{1-6}$ alkyl. In some embodiments, $R^5$, $R^6$, and $R^7$ may be H.

With respect to any relevant formula or structural depiction above, $R^8$ may be H or any substituent. Some non-limiting examples of $R^8$ may include $R^A$, F, Cl, CN, $OR^A$, $CF_3$, $NO_2$, $NR^AR^B$, $COR^A$, $CO_2R^A$, $OCOR^A$, etc. In some embodiments, $R^8$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^8$ may be H.

With respect to any relevant formula or structural depiction above, in some embodiments, $R^5$, $R^6$, $R^7$, and $R^8$ may independently be H, $C_{1-6}$ alkyl, or —O—$C_{1-6}$ alkyl. In some embodiments, $R^5$, $R^6$, $R^7$, and $R^8$ may be H.

With respect to any relevant formula or structural depiction above, $R^9$ may be H or any substituent. Some non-limiting examples of $R^9$ may include $R^A$, F, Cl, CN, $OR^A$, $CF_3$, $NO_2$, $NR^AR^B$, $COR^A$, $CO_2R^A$, $OCOR^A$, etc. In some embodiments, $R^9$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^9$ may be H.

With respect to any relevant formula or structural depiction above, $R^{10}$ may be H or any substituent. Some non-limiting examples of $R^{10}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{10}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{10}$ may be H.

With respect to any relevant formula or structural depiction above, $R^{11}$ may be H or any substituent. Some non-limiting examples of $R^{11}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{11}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{11}$ may be H.

With respect to any relevant formula or structural depiction above, in some embodiments, $R^9$, $R^{10}$, and $R^{11}$ may independently be H, $C_{1-6}$ alkyl, or —O—$C_{1-6}$ alkyl. In some embodiments $R^9$, $R^{10}$, and $R^{11}$ may be H.

With respect to any relevant formula or structural depiction above, $R^{12}$ may be H or any substituent. Some non-limiting examples of $R^{12}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{12}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{12}$ may be H.

With respect to any relevant formula or structural depiction above, in some embodiments, $R^9$, $R^{10}$, $R^{11}$, and $R^{12}$ may independently be H, $C_{1-6}$ alkyl, or —O—$C_{1-6}$ alkyl. In some embodiments, $R^9$, $R^{10}$, $R^{11}$, and $R^{12}$ may be H.

With respect to any relevant formula or structural depiction above, $R^{13}$ may be H or any substituent. Some non-limiting examples of $R^{13}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{13}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{13}$ may be H.

With respect to any relevant formula or structural depiction above, $R^{14}$ may be H or any substituent. Some non-limiting examples of $R^{14}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{14}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{14}$ may be H.

With respect to any relevant formula or structural depiction above, $R^{15}$ may be H or any substituent. Some non-limiting examples of $R^{15}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{15}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{15}$ may be H.

With respect to any relevant formula or structural depiction above, $R^{16}$ may be H or any substituent. Some non-limiting examples of $R^{16}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{16}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{16}$ may be H.

With respect to any relevant formula or structural depiction above, in some embodiments, $R^{13}$, $R^{14}$, $R^{15}$, and $R^{16}$ may independently be H, $C_{1-6}$ alkyl, or —O—$C_{1-6}$ alkyl. In some embodiments, $R^{13}$, $R^{14}$, $R^{15}$, and $R^{16}$ may be H.

With respect to any relevant formula or structural depiction above, $R^{17}$ may be H or any substituent. Some non-limiting examples of $R^{17}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{17}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{17}$ may be H.

With respect to any relevant formula or structural depiction above, $R^{18}$ may be H or any substituent. Some non-limiting examples of $R^{18}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{18}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{18}$ may be H.

With respect to any relevant formula or structural depiction above, $R^{19}$ may be H or any substituent. Some non-limiting examples of $R^{19}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{19}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{19}$ may be H.

With respect to any relevant formula or structural depiction above, $R^{20}$ may be H or any substituent. Some non-limiting examples of $R^{20}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{20}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{20}$ may be H.

With respect to any relevant formula or structural depiction above, $R^{21}$ may be H or any substituent. Some non-limiting examples of $R^{21}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{21}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{21}$ may be H.

With respect to any relevant formula or structural depiction above, in some embodiments, $R^{13}$, $R^{14}$, $R^{15}$, $R^{16}$, $R^{17}$, $R^{18}$, $R^{19}$, $R^{20}$, and $R^{21}$ may independently be H, $C_{1-6}$ alkyl, or —O—$C_{1-6}$ alkyl. In some embodiments, $R^{13}$, $R^{14}$, $R^{15}$, $R^{16}$, $R^{17}$, $R^{18}$, $R^{19}$, $R^{20}$, and $R^{21}$ may be H.

With respect to any relevant formula or structural depiction above, $R^{22}$ may be H or any substituent. Some non-limiting examples of $R^{22}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{22}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{22}$ may be H.

With respect to any relevant formula or structural depiction above, $R^{23}$ may be H or any substituent. Some non-limiting examples of $R^{23}$ may include $R^A$, F, Cl, CN, $OR^A$, $CF_3$, $NO_2$, $NR^AR^B$, $COR^A$. $CO_2R^A$, $OCOR^A$, etc. In some embodiments, $R^{23}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{23}$ may be H.

With respect to any relevant formula or structural depiction above, $R^{24}$ may be H or any substituent. Some non-limiting examples of $R^{24}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{24}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{24}$ may be H.

With respect to any relevant formula or structural depiction above, $R^{25}$ may be H or any substituent. Some non-limiting examples of $R^{25}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{25}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{25}$ may be H.

With respect to any relevant formula or structural depiction above, in some embodiments, $R^{22}$, $R^{23}$, $R^{24}$, and $R^{25}$ may independently be H, $C_{1-6}$ alkyl, and —$C_{1-6}$ alkyl. In some embodiments, $R^{22}$, $R^{23}$, $R^{24}$, and $R^{25}$ may be H.

With respect to any relevant formula or structural depiction above, $R^{26}$ may be H or any substituent. Some non-limiting examples of $R^{26}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{26}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{26}$ may be H.

With respect to any relevant formula or structural depiction above, $R^{27}$ may be H or any substituent. Some non-limiting examples of $R^{27}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{27}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{27}$ may be H.

With respect to any relevant formula or structural depiction above, $R^{28}$ may be H or any substituent. Some non-limiting examples of $R^{28}$ may include $R^A$, F, Cl, CN, $OR^A$, $CF_3$, $NO_2$, $NR^AR^B$, $COR^A$, $CO_2R^A$. $OCOR^A$, etc. In some embodiments, $R^{28}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{28}$ may be H.

With respect to any relevant formula or structural depiction above, $R^{29}$ may be H or any substituent. Some non-limiting examples of $R^{29}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{29}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{29}$ may be H.

With respect to any relevant formula or structural depiction above, $R^{30}$ may be H or any substituent. Some non-limiting examples of $R^{30}$ may include $R^A$, F, Cl, CN, $OR^A$, $CF_3$, $NO_2$, $NR^AR^B$, $COR^A$, $CO_2R^A$, $OCOR^A$, etc. In some embodiments, $R^{30}$ may be H, $C_{1-6}$ alkyl, such as methyl, ethyl, propyl isomers, cyclopropyl, butyl isomers, cyclobutyl isomers, pentyl isomers, cyclopentyl isomers, hexyl isomers, cyclohexyl isomers, etc., or —O—$C_{1-6}$ alkyl, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc. In some embodiments, $R^{30}$ may be H.

With respect to any relevant formula or structural depiction above, in some embodiments, $R^{22}$, $R^{23}$, $R^{24}$, $R^{25}$, $R^{26}$, $R^{27}$, $R^{28}$, $R^{29}$, and $R^{30}$ may independently be H, $C_{1-6}$ alkyl or $C_{1-6}$—O-alkyl. In some embodiments, $R^{22}$, $R^{23}$, $R^{24}$, $R^{25}$, $R^{26}$, $R^{27}$, $R^{28}$, $R^{29}$, and $R^{30}$ may be H.

Some examples of useful compounds include, but are not limited to, the compounds below.

Compound-3

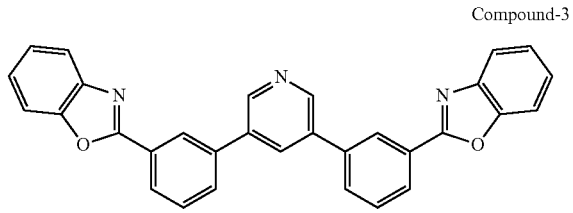

Compound-8

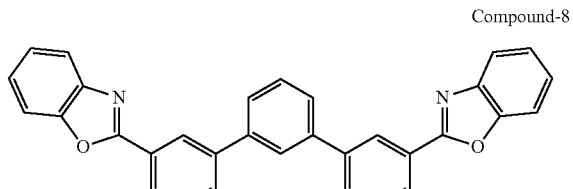

Compound-9

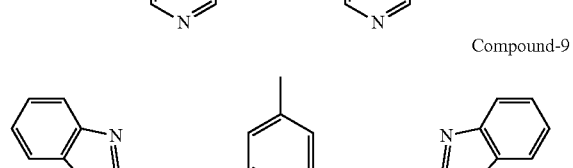

Compound-12

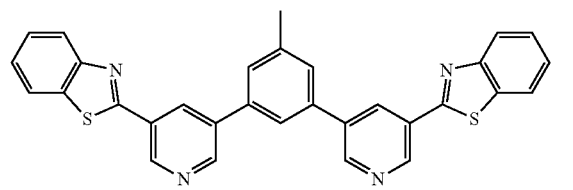

Compound-15

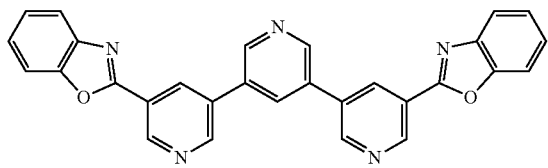

Compound-18

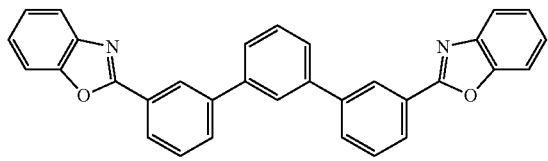

A porous film may comprise any of the compounds described herein. A porous film comprising a compound described herein may be useful in a variety of devices involving the transmission of light from one layer to another, such as light-emitting diodes, photovoltaics, detectors, etc. In some embodiments, a porous film may provide efficient light outcoupling for organic light-emitting diodes for uses such as lighting. With some devices, light extraction from a substrate close to 90%, or possibly greater, may be achieved. The porous films may provide easy processing and potentially low cost improvement in device efficiency.

In some embodiments, the porous films described herein may improve efficiency of a device by reducing the amount of total internal reflection in a layer of the device. Total internal reflection may be a significant cause of trapping. When light passes from a high refractive index material to a low refractive index material, the light may be bent in a direction away from the normal angle to the interface. If light in a higher refractive index material encounters an interface with a lower refractive index material at an angle which deviates substantially from 90°, the bending of the light may be greater than the angle at which the light approaches the interface, so that instead of passing out of the higher refractive index material, the light may be bent back into the higher refractive index material. This may be referred to as total internal reflection. Since air may have a lower refractive index than many materials, many interfaces between a device and air may suffer from loss due to total internal reflection. Furthermore, trapping due to total internal reflection may occur at any interface in a device where the light travels from a higher refractive index layer to a lower refractive index layer. Devices comprising porous films describe herein may have reduced total internal reflection or trapping and thus have improved efficiency.

In some embodiments, a porous film described herein may provide light scattering for a variety of devices that involve light passing from one material to another, including devices that absorb or emit light. Light scattering may be useful in a device to provide viewing angle color consistency, so that the color is substantially similar regardless of the angle from which light is viewed. Devices having no light scattering layer may emit light in such a way that the viewer observes a different color depending upon the angle from which the light is viewed.

In some embodiments, a porous film described herein may also be useful as a filter for a variety of devices that involve light passing from one material to another, including devices that absorb or emit light.

The thickness of a porous film may vary. In some embodiments, a porous film may have a thickness in the nanometer to micrometer range. For example, the thickness of the film may be about 500 nm, about 0.1 µm, about 1 µm, about 1.3 µm, about 3 µm, or about 4 µm, about 5 µm, about 7 µm, about 10 µm, about 20 µm, about 100 µm, or any thickness in a range bounded by, or between, any of these values. In some embodiments, the thickness of the film may be about 500 nm to about 100 µm, about 0.1 µm to about 10 µm, or about 1 µm to about 5 µm.

A porous film may comprise a number of pores or voids. For example, a porous film may comprises a plurality of voids having a total volume that may be about 50%, about 70%, about 80%; about 85%, about 90%, about 95%, or about 99% of the volume of the film including the voids, or any percentage of total volume in a range bounded by, or between, any of these values. Thus, if the total volume of the voids is 50% of the volume of the film, 50% of the volume of the film is the material of the film and 50% of the volume of the film is the plurality of voids. In some embodiments, the porous film may comprise a plurality of voids having a total volume that may be about 50% to about 99%, about 70% to about 99%, about 80% to about 99%, or about 90% to about 99% of the volume of the film.

In some embodiments, a film may comprises a plurality of voids of a number and size such that the film may have a thickness that is about 2 times, about 10 times; up to about 50 times, or about 100 times, that of the thickness of a film of the same material which has no voids, or any thickness ratio in a range bounded by, or between, any of these values. For example, a film may have a thickness of about 5 µm when a film of the same material would have a thickness of 800 nm if the film had no voids. In some embodiments, the film may have a thickness that is in the range of about 2 times to about 100 times or about 2 to about 10 times that of the thickness of a film of the same material which has no voids.

The density of a porous film may vary, and may be affected by the voids, the material, and other factors. In some embodiments, the density of the film including the voids may be about 0.005 picograms/µm$^3$, about 0.05 picograms/µm$^3$, about 0.1 picograms/µm$^3$, about 0.3 picograms/µm$^3$, about 0.5 picograms/µm$^3$, about 0.7 picograms/µm$^3$, about 0.9 picograms/µm$^3$, or any density in a range bounded by, or between, any of these values. In some embodiments, the including the voids may be in the range of about: about 0.005 picograms/µm$^3$ to about 0.9 picograms/µm$^3$, about 0.05 picograms/µm$^3$ to about 0.7 picograms/µm$^3$, or about 0.1 picograms/µm$^3$ to about 0.5 picograms/µm$^3$.

A porous film may be prepared by depositing a material comprising a compound disclosed herein on a surface, such as a substrate. For example, the deposition may be vapor deposition, which may be carried out under high temperature and/or high vacuum conditions; or the porous film may be deposited by drop casting or spin casting. In some embodiments, the material may be deposited on a substantially transparent substrate. Deposition and/or annealing conditions may affect the characteristics of the film.

The rate of deposition of the material on a surface may vary. For example, the deposition rate may be: about 0.1 Å/sec, about 0.2 Å/sec, about 1 Å/sec, about 10 Å/sec, about 100 Å/sec, about 500 Å/sec, about 1000 Å/sec, or any value in a range bounded by, or between, any of these deposition rates. In some embodiments, the organic film may be deposited at a rate in the range of about 0.1 Å/sec to about 1000 Å/sec, about 1 Å/sec to about 100 Å/sec, or about 2 Å/sec to about 60 Å/sec. The material may be deposited onto a variety of surfaces to form a film. For some devices, the material may be deposited onto an anode, a cathode, or a transparent layer.

A material that has been deposited on a surface may be further treated by heating or annealing. The temperature of heating may vary. For example, the a precursor material may be heated at a temperature of about 80° C., about 100° C., about 110° C., about 120° C., about 150° C., about 180° C., about 200° C., about 130° C., about 260° C., about 290° C., or any temperature in a range bounded by, or between, any of these values. In some embodiments, a material may be heated at a temperature in the range of about 100° C. to about 290° C., about 100° C. to about 260° C., about 80° C. to about 240° C., about 80° C. to about 200° C., about 200° C. to about 260° C., or about 200° C. to about 240° C.

The time of heating may also vary. For example, the material may be heated for about 5 minutes, about 15 minutes, about 30 minutes, about 60 minutes, about 2 hours, about 5 hours, about 10 hours, about 20 hours, or any amount of time in a range bounded by, or between, any of these values. In some embodiments, an organic film may be heated for about 5 minutes to about 20 hours, about 4 minutes to about 2 hours, or about 5 minutes to about 30 minutes. In some embodiments, a material may be heated at about 100° C. to about 260° C. for about 5 minutes to about 30 minutes.

In some embodiments a porous film may comprise COMPOUND-3 and may have a density of about 80% and/or a thickness greater than about 4 μm. In some embodiments, COMPOUND-3 may be heated at about 110° C. and/or heating may be carried out for about 60 min.

In some embodiments a porous film may comprise COMPOUND-8 and may have a thickness of about 1.3 μm. In some embodiments, COMPOUND-8 may be heated at about 180° C. and/or heating may be carried out for about 15 minutes.

Generally, a porous film may be deposited on at least part of a surface of a layer in a device to provide an outcoupling or a scattering effect. For outcoupling, a porous film may be deposited on at least part of a surface of any partially internally reflective layer, including any layer that may both reflect light and allow light to pass through the partially internally reflective layer to an adjacent layer, such as an emissive layer, an anode, a cathode, any transparent layer, etc. In some embodiments, a transparent layer may be disposed between the anode and the film, the cathode and the film, etc.

A light-emitting device comprising a porous film may have a variety of configurations. For example, a light emitting device may include an anode, a cathode and an emissive layer disposed between the anode and cathode.

With respect to the devices described herein, if a first layer is "disposed over" a second layer, the first layer covers at least a portion of the second layer, but optionally allows one or more additional layers to be positioned between the two layers. If a first layer is "disposed on" a second layer, the first layer makes direct contact with at least a portion of the second layer. For simplicity, in any situation where the "disposed over" is used herein, it should be understood to mean "disposed over or disposed on."

Figure 2:
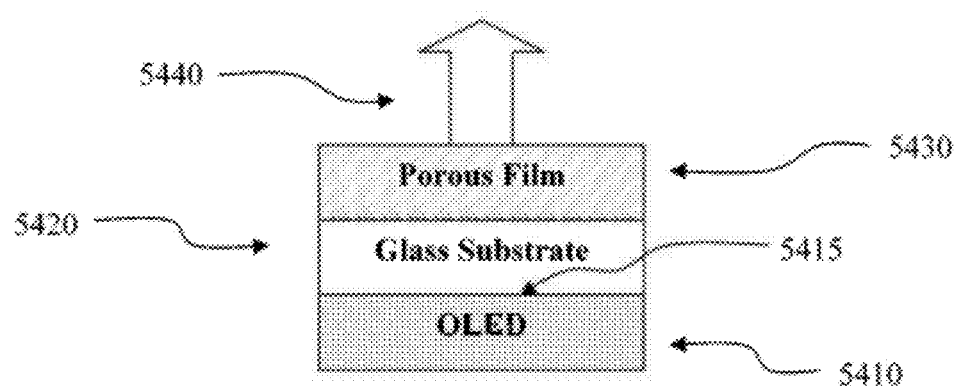
FIG. 2 is a schematic diagram of some embodiments of a device described herein.

With reference to FIGS. 1 and 2, a porous film 5430 may be disposed over the emitting surface 5415 of an OLED 5410. In some embodiments, the porous film 5430 is disposed directly on the emitting surface 5415 of an OLED 5410 (FIG. 1) and functions as an outcoupling film. Emitted light 5440 from the OLED 5410 may pass through the porous film 5430. In some embodiments, a glass substrate 5420 may be disposed between the OLED 5410 and the porous film 5430, wherein the glass substrate 5420 is in contact with or adjacent to the light emitting surface 5415 of the OLED 5410. Emitted light 5440 may pass from the OLED 5410 through the glass substrate 5420 and out of the porous film 5430. The porous film 5430 functions as an outcoupling film.

Figure 3:
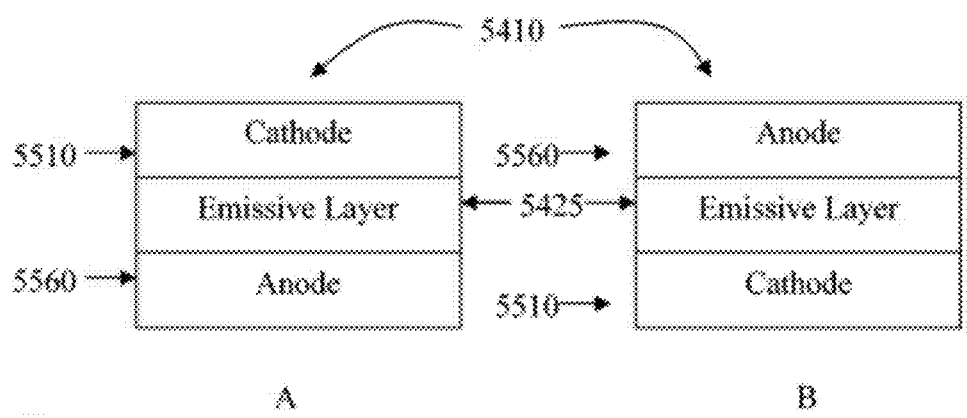
FIG. 3 is a schematic diagram of some embodiments of a device described herein.

The OLED 5410 that is suitable for the devices described above generally comprises an emissive layer 5425 disposed between an anode 5560 and a cathode 5510. Other layers, such as an electron-transport layer, a hole-transport layer, an electron-injection layer, a hole-injection layer, an electron-blocking layer, a hole-blocking layer, additional emissive layers, etc., may be present between the emissive layer 5425, and the anode 5560 and/or the cathode 5510. With reference to FIG. 3A, an emissive layer 5425 is disposed over an anode 5560, and a cathode 5510 is disposed over an emissive layer 5425. Light may be emitted from the top and/or the bottom of the device. FIG. 3B depicts an example wherein an emissive layer 5425 may be disposed over a cathode 5510, and an anode 5560 may be disposed over the emissive layer 5425. Light may be emitted from the top and/or the bottom of the device.

In some embodiments, an outcoupling film or porous layer 5430 described herein may be disposed over the anode 5560 or the cathode 5510, so that light passes through the anode or the cathode, any intervening layers (if present), and through the outcoupling film or porous layer 5430. In some embodiments, a transparent substrate or a glass substrate may be disposed between the anode 5560 and the porous layer 5430, or between the cathode 5510 and the porous layer 5430. In some embodiments, the porous layer 5430 is disposed on the transparent substrate. The transparent substrate is disposed on the anode 5560 if the light is emitted from the OLED through the anode 5560. In other embodiments, the transparent substrate is disposed on the cathode 5510 when the light is emitted from the OLED through the cathode 5510.

Figure 4:
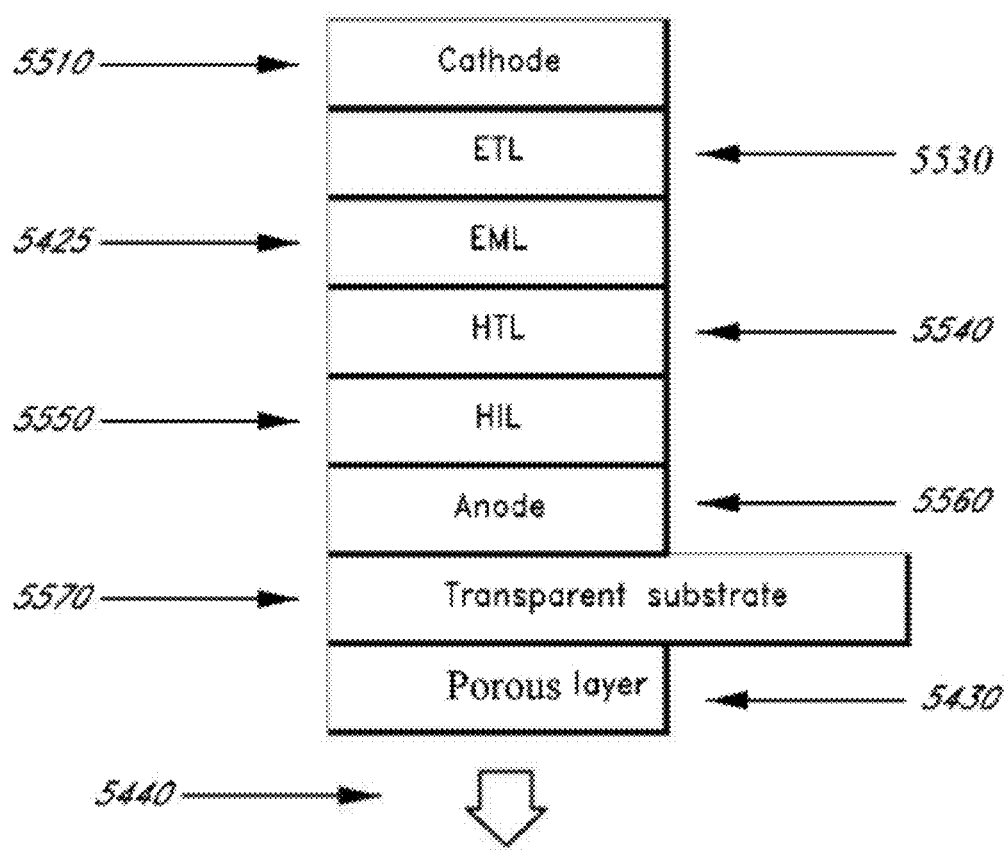
FIG. 4 is a schematic diagram of some embodiments of a device described herein.

In some embodiments, additional layers may be present between the emissive layer 5425 and the anode 5560 or between the emissive layer 5425 and the cathode 5510. With reference to FIG. 4, an electron-transport layer 5530 may be disposed between the emissive layer 5425 and the cathode 5510, a hole-injection layer 5550 may be disposed between the emissive layer 5425 and the anode 5560, and a hole-transport layer 5540 may be disposed between the emissive layer 5425 and the hole-injection layer 5550. When the light is emitted from the anode 5560 side, a porous layer 5430 may be disposed over the anode 5560. In some embodiments, a transparent substrate 5570 may be disposed between the anode 5560 and the porous layer 5430. Light emitted by the emissive layer 5425 may pass through the hole-transport layer 5540, the hole-injection layer 5550, the anode 5560, the transparent substrate 5570, and the porous film 5430 to provide light 5440 emitted by the device through the bottom of the device.

Figure 5:
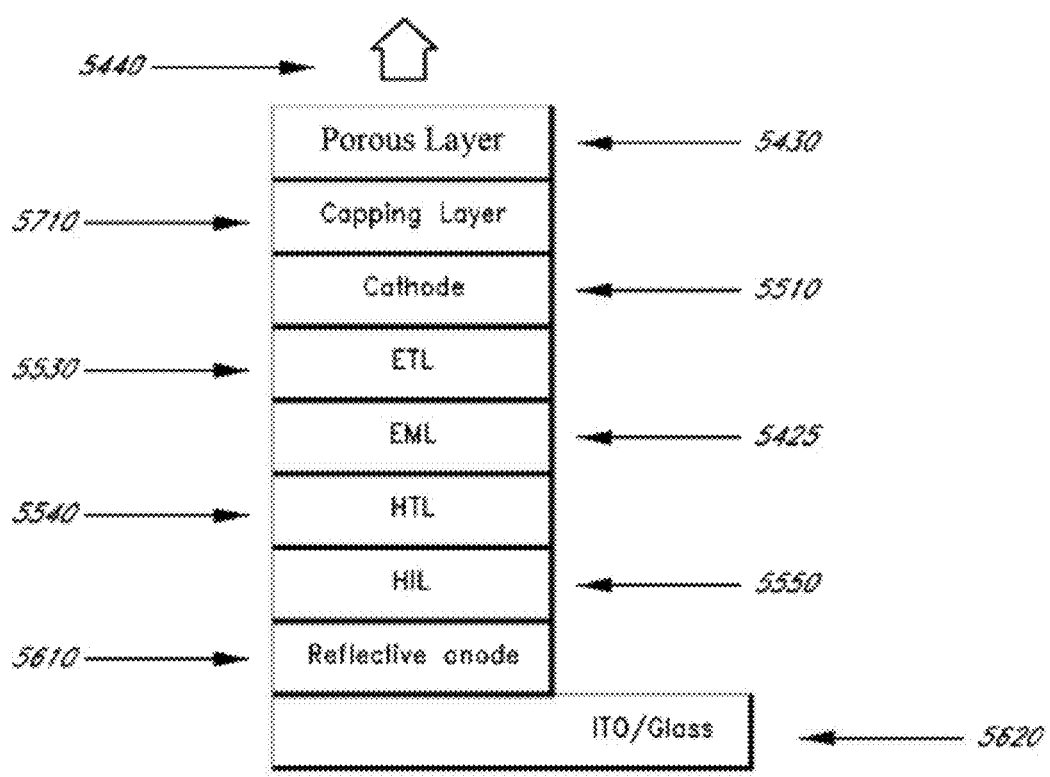
FIG. 5 is a schematic diagram of some embodiments of a device described herein.

In some embodiments, the anode may be reflective and the light may be emitted from the cathode 5510 side. With reference to FIG. 5, an electron-transport layer 5530 may be disposed between the emissive layer 5425 and the cathode 5510, a hole-injection layer 5550 may be disposed between the emissive layer 5425 and the reflective anode 5610, and a hole-transport layer 5540 may be disposed between the emissive layer 5425 and the hole-injection layer 5550. A capping layer 5710 may be disposed on the cathode 5510. A porous layer 5430 can be disposed over the cathode 5510. In some embodiments, a capping layer 5710 may be disposed on the cathode 5510, between the cathode 5510 and the porous layer 5430. Light that is emitted by the emissive layer 5425, may pass through the electron-transport layer 5530, the cathode 5510, the capping layer 5710, and the porous film 5430 to provide light 5440 emitted by the device through the top of the device. In some embodiments, the OLED device may be disposed on a substrate 5620, such as an indium tin oxide (ITO)/glass substrate. In the embodiments where a reflective anode 5610 is present, the substrate 5620 may be in contact with or adjacent to the reflective anode 5610. Light that may be emitted by the emissive layer 5425, may pass through the electron-transport layer 5530, the cathode 5510, the capping layer 5710, and the porous film 5430 to provide light 5440 emitted by the device through the top of the device.

Figure 6:
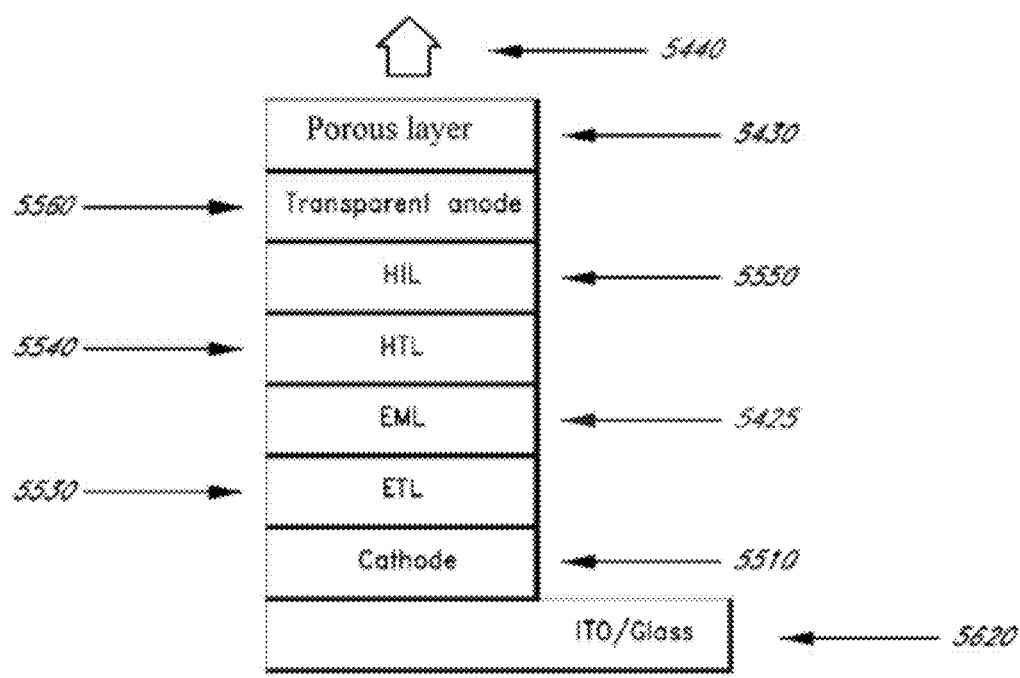
FIG. 6 is a schematic diagram of some embodiments of a device described herein.

In some embodiments, the light may be emitted through a transparent anode 5560. With reference to FIG. 6, an emissive layer 5425 is disposed between the cathode 5510 and the transparent anode 5560. A porous film or layer 5430 is disposed on the transparent anode 5560. In some embodiments, an electron-transport layer 5530 may be disposed between the emissive layer 5425 and the cathode 5510, a hole-injection layer 5550 may be disposed between the emissive layer 5425 and the transparent anode 5560, and a hole-transport layer 5540 may be disposed between the emissive layer 5425 and the hole-injection layer 5550. In some embodiments, the OLED may be disposed on a substrate 5620, such as an indium tin oxide (ITO)/glass substrate. The substrate 5620 may be in contact with or adjacent to the cathode 5510. Light may be emitted by the emissive layer 5425 and pass through the hole-transport layer 5540, the hole-injection layer 5550, the anode 5560, and the porous film 5430 to provide light 5440 emitted through the top of the device.

An anode may be a layer comprising a conventional material such as a metal, a mixed metal, an alloy, a metal oxide or a mixed-metal oxide, a conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). Examples of suitable high work function metals and metal oxides include but are not limited to Au, Pt, or alloys thereof; ITO; IZO; and the like. In some embodiments, the anode layer can have a thickness in the range of about 1 nm to about 1000 nm.

A cathode may be a layer including a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and Li$_2$O may also be deposited between the emissive layer and the cathode layer to lower the operating voltage. In some embodiments a cathode may comprise Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

A transparent electrode may include an anode or a cathode through which some light may pass. In some embodiments, a transparent electrode may have a relative transmittance of about 50%, about 80%, about 90%, about 100%, or any transmittance in a range bounded by, or between, any of these values. In some embodiments, a transparent electrode may have a relative transmittance of about 50% to about 100%, about 80% to about 100%, or about 90% to about 100%.

An emissive layer may be any layer that can emit light. In some embodiments, an emissive layer may comprise an emissive component, and optionally, a host. The device may be configured so that holes can be transferred from the anode to the emissive layer and/or so that electrons can be transferred from the cathode to the emissive layer. If present, the amount of the host in an emissive layer may vary. For example, the host may be about 50%, about 60%, about 90%, about 97%, or about 99% by weight of the emissive layer, or may be any percentage in a range bounded by, or between, any of these values. In some embodiments, the host may be about 50% to about 99%, about 90% to about 99%, or about 97% to about 99% by weight of the emissive layer.

In some embodiments, Compound-13 may be a host in an emissive layer.

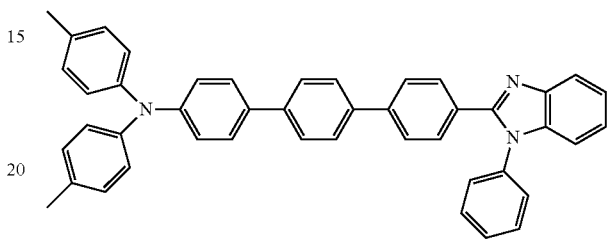

Compound-13

The amount of an emissive component in an emissive layer may vary. For example, the emissive component may be about 0.1%, about 1%, about 3%, about 5%, about 10%, or about 100% of the weight of the emissive layer, or may be any percentage in a range bounded by, or between, any of these values. In some embodiments, the emissive layer may be a neat emissive layer, meaning that the emissive component is about 100% by weight of the emissive layer, or alternatively, the emissive layer consists essentially of emissive component. In some embodiments, the emissive component may be about 0.1% to about 10%, about 0.1% to about 3%, or about 1% to about 3% by weight of the emissive layer.

The emissive component may be a fluorescent and/or a phosphorescent compound. In some embodiments, the emissive component comprises a phosphorescent material. Some non-limiting examples of emissive compounds may include: bis-{4-phenylthieno[4,2-c]pyridinato-N,C2'}iridium(III) (acetylacetonate) (PO-01), bis-{2-[3,5-bis(trifluoromethyl)phenyl]pyridinato-N,C2'}iridium(III)-picolinate, bis(2-[4,6-difluorophenyl]pyridinato-N,C2')iridium(III)picolinate, bis (2-[4,6-difluorophenyl]pyridinato-N,C2')iridium (acetylacetonate), Iridium(III)bis(4,6-difluorophenylpyridinato)-3-(trifluoromethyl)-5-(pyridine-2-yl)-1,2,4-triazolate, Iridium(III) bis(4,6-difluorophenylpyridinato)-5-(pyridine-2-yl)-1H-tetrazolate, bis[2-(4,6-difluorophenyl)pyridinato-N,C$^{2'}$]iridium(III)tetra (1-pyrazolyl)borate, Bis[2-(2'-benzothienyl)-pyridinato-N,C3']iridium(III)(acetylacetonate); Bis[(2-phenylquinolyl)-N,C2']iridium(III) (acetylacetonate); Bis[(1-phenylisoquinolinato-N,C2')]iridium(III) (acetylacetonate); Bis[(dibenzo[f,h]quinoxalino-N,C2')iridium(III)(acetylacetonate); Tris(2,5-bis-2'-(9',9'-dihexylfluorene)pyridine)iridium(III); Tris[1-phenylisoquinolinato-N,C2']iridium(III); Tris-[2-(2'-benzothienyl)-pyridinato-N,C3']iridium(III); Tris [1-thiophen-2-ylisoquinolinato-N,C3']iridium(III); and Tris [1-(9,9-dimethyl-9H-fluoren-2-yl)isoquinolinato-(N,C3')iridium (III)), Bis(2-phenylpyridinato-N,C2')iridium(III) (acetylacetonate) [Ir(ppy)$_2$(acac)], Bis(2-(4-tolyl)pyridinato-N,C2')iridium(III)(acetylacetonate) [Ir(mppy)$_2$(acac)], Bis (2-(4-tert-butyl)pyridinato-N,C2')iridium(III) (acetylacetonate) [Ir(t-Buppy)$_2$(acac)], Tris(2-phenylpyridinato-N,C2')iridium(III) [Ir(ppy)$_3$], Bis(2-phenyloxazolinato-N,C2')iridium(III) (acetylacetonate) acetonate) [Ir(op)$_2$(acac)], Tris(2-(4-tolyl)pyridinato-N,C2') iridium(III) [Ir(mppy)$_3$], Bis[2-phenylbenzothiazolato-N, C2']iridium(III)(acetylacetonate), Bis[2-(4-tert-butylphenyl)benzothiazolato-N,C2']iridium(III)(acetylacetonate), Bis[(2-(2'-thienyl)pyridinato-N,C3')]iridium(III) (acetylacetonate), Tris[2-(9,9-dimethylfluoren-2-yl)pyridinato-(N,C3')]iridium(III), Tris[2-(9,9-dimethylfluoren-2-yl)pyridinato-(N,C3')]iridium(III), and Bis[5-trifluoromethyl-2-[3-(N-phenyl-carbzolyl)pyridinato-N,C2']iridium(III)(acetylacetonate), (2-PhPyCz)₂Ir(III)(acac), etc.

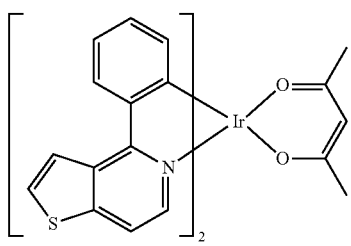

PO-01
bis-{4-phenylthieno[4,2-c]pyridinato-N, C2'}
iridium (III)(acetylacetonate)

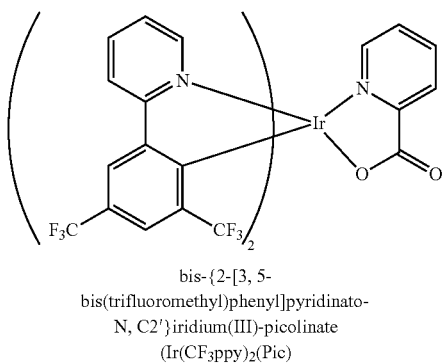

bis-{2-[3, 5-bis(trifluoromethyl)phenyl]pyridinato-
N, C2'}iridium(III)-picolinate
(Ir(CF₃ppy)₂(Pic)

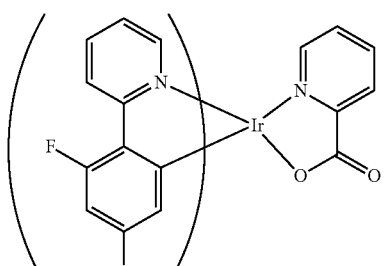

bis(2-[4,6-difluorophenyl]pyridinato-
N, C2')iridium (III) picolinate [FIrPic]

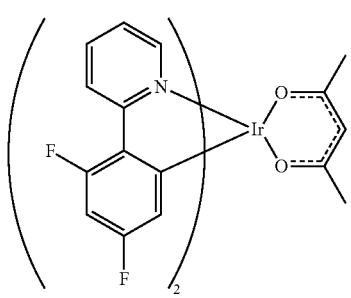

bis(2-[4,6-difluorophenyl]pyridinato-
N, C2')iridium(acetylacetonate) [FIr(acac)]

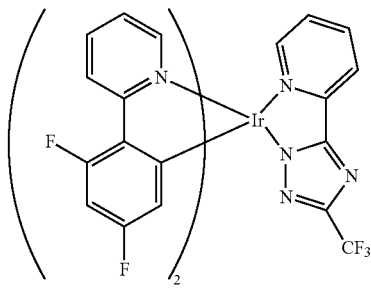

Iridium (III) bis(4,6-difluorophenylpyridinato)-3-(trifluoromethyl)-5-(pyridine-2-yl)-1,2,4-triazolate (FIrtaz)

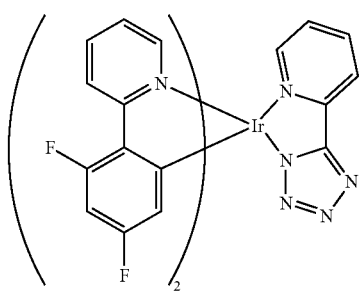

Iridium (III) bis(4,6-difluorophenylpyridinato)-5-(pyridine-2-yl)-1H-tetrazolate (FIrN4)

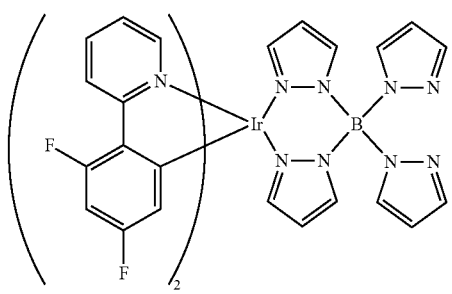

bis[2-(4,6-difluorophenyl)pyridinato-N,C2']iridium(III)tetra(1-pyrazolyl)borate
(Fir6)

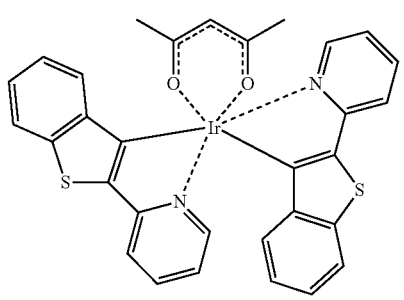

Ir(btp)₂(acac) 1

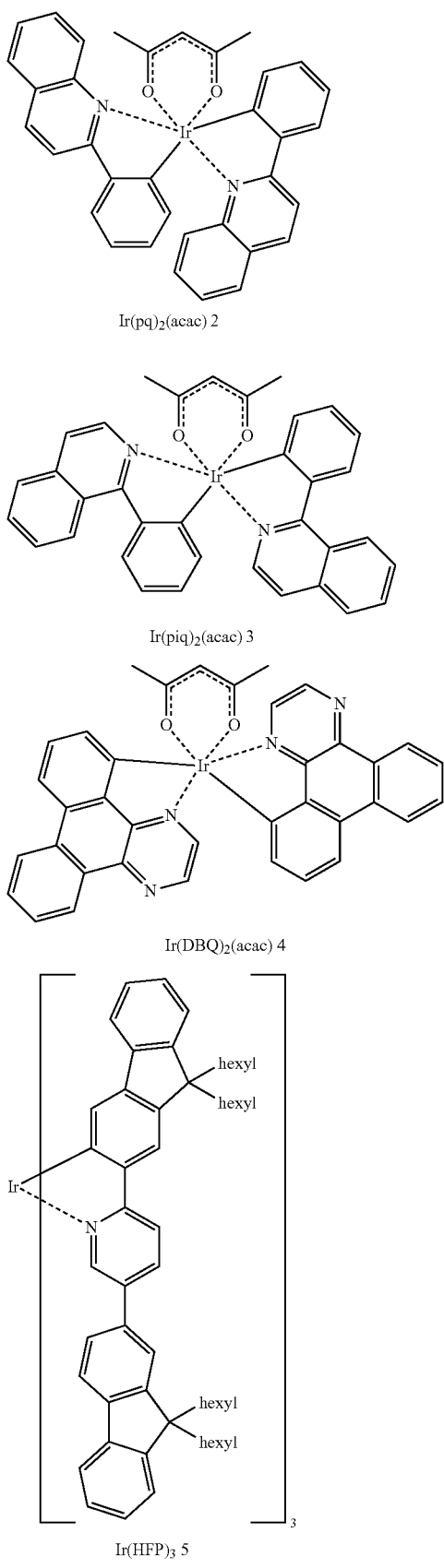
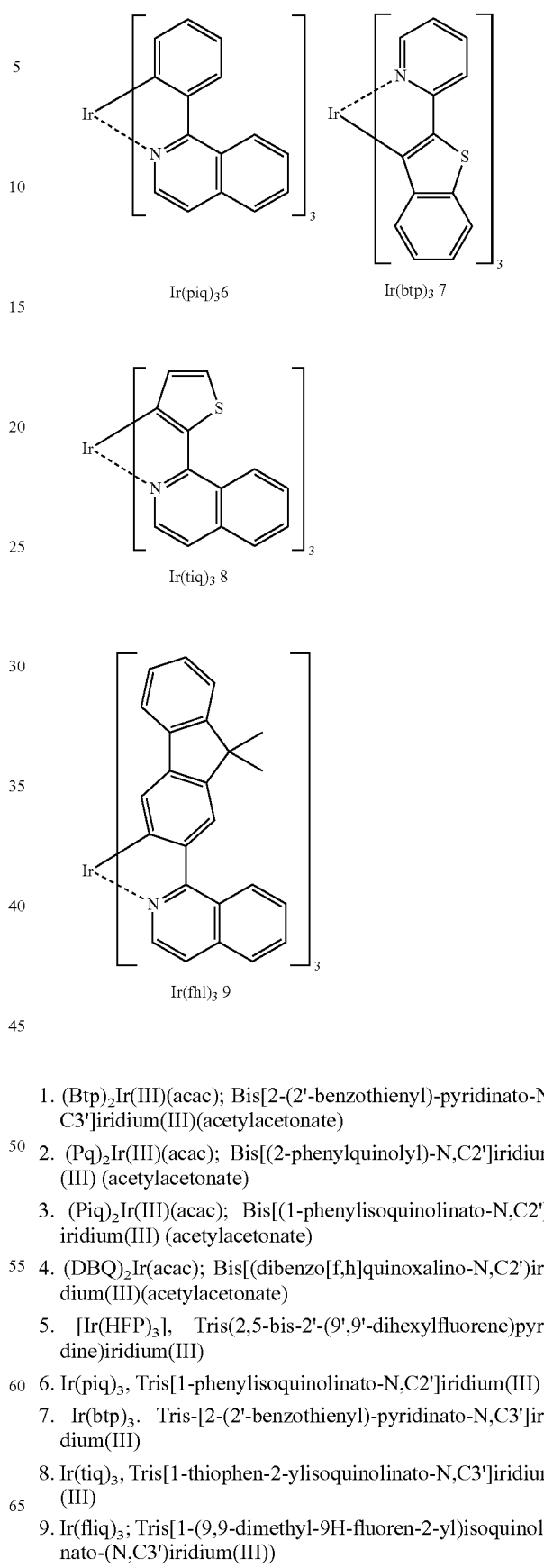

1. (Btp)₂Ir(III)(acac); Bis[2-(2'-benzothienyl)-pyridinato-N, C3']iridium(III)(acetylacetonate)
2. (Pq)₂Ir(III)(acac); Bis[(2-phenylquinolyl)-N,C2']iridium (III) (acetylacetonate)
3. (Piq)₂Ir(III)(acac); Bis[(1-phenylisoquinolinato-N,C2')] iridium(III) (acetylacetonate)
4. (DBQ)₂Ir(acac); Bis[(dibenzo[f,h]quinoxalino-N,C2')iridium(III)(acetylacetonate)
5. [Ir(HFP)₃], Tris(2,5-bis-2'-(9',9'-dihexylfluorene)pyridine)iridium(III)
6. Ir(piq)₃, Tris[1-phenylisoquinolinato-N,C2']iridium(III)
7. Ir(btp)₃, Tris-[2-(2'-benzothienyl)-pyridinato-N,C3']iridium(III)
8. Ir(tiq)₃, Tris[1-thiophen-2-ylisoquinolinato-N,C3']iridium (III)
9. Ir(fliq)₃; Tris[1-(9,9-dimethyl-9H-fluoren-2-yl)isoquinolinato-(N,C3')iridium(III))

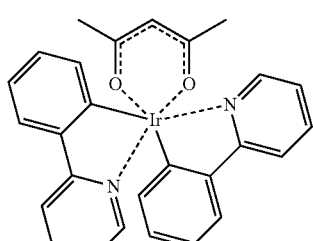
Ir(ppy)₂(acac)
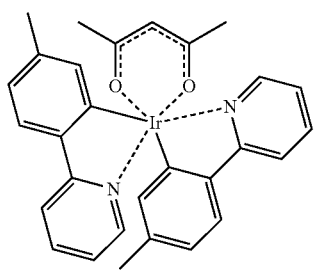
Ir(mppy)₂(acac)
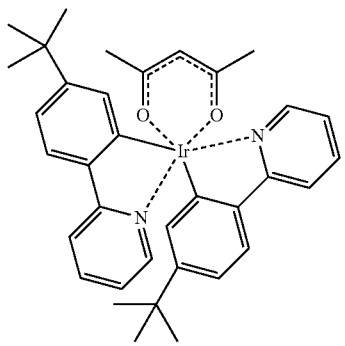
Ir(t-Buppy)₂(acac)
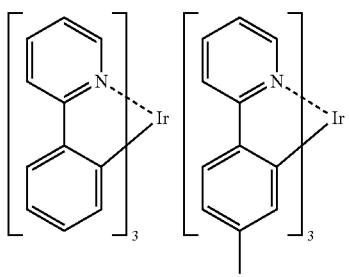
Ir(ppy)₃   Ir(mppy)₃
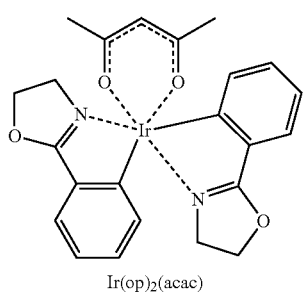
Ir(op)₂(acac)
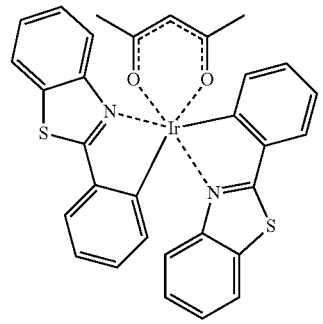
(bt)₂Ir(III)(acac)
Bis[2-phenylbenzothiazolato-N, C2'] iridium (III)(acetylacetonate)
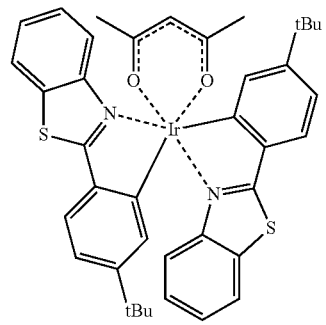
(t-bt)₂Ir(III)(acac)
Bis[2-(4-tert-butylphenyl)benzothiazolato-N, C2']iridium (III)(acetylacetonate)
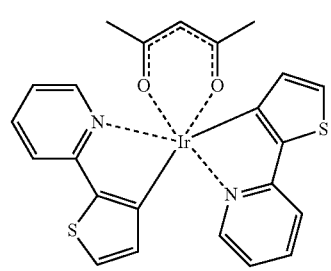
(thp)₂Ir(III)(acac)
Bis[(2-(2'-thienyl)pyridinato-N, C3')]iridium (III) (acetylacetonate)

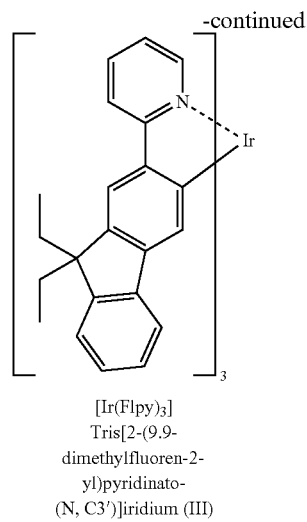

[Ir(Flpy)₃]
Tris[2-(9,9-dimethylfluoren-2-yl)pyridinato-
(N, C3')]iridium (III)

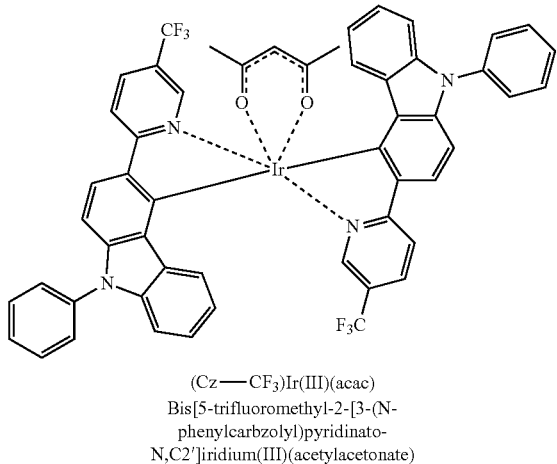

(Cz—CF₃)Ir(III)(acac)
Bis[5-trifluoromethyl-2-[3-(N-phenylcarbzolyl)pyridinato-
N,C2']iridium(III)(acetylacetonate)

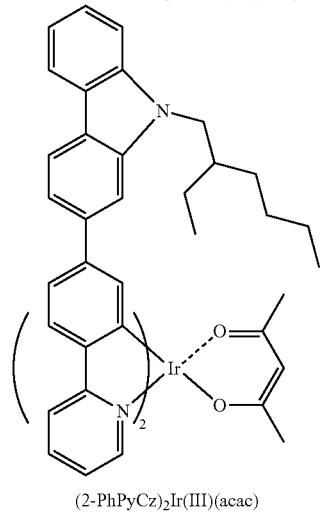

(2-PhPyCz)₂Ir(III)(acac)

The thickness of an emissive layer may vary. In some embodiments, an emissive layer may have a thickness in the range of about 1 nm to about 150 nm or about 200 nm.

A hole-transport layer may comprise at least one hole-transport material. Examples of hole-transport materials may include: an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-berizothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; copper phthalocyanine; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4'-tris(3-methylphenylphenylamino)triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPD); 4,4',4"-tris(carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); Bis[4-(p,p'-ditolyl-amino)phenyl]diphenylsilane (DTASi); 2,2'-bis(4-carbazolylphenyl)-1,1'-biphenyl (4CzPBP); N,N'N"-1,3,5-tricarbazoloylbenzene (tCP); N,N'-bis(4-butylphenyl)-N,N'-bis(phenyl)benzidine; a combination thereof; or any other material known in the art to be useful as a hole-transport material.

An electron-transport layer may comprise at least one electron-transport material. Examples of electron-transport materials may include: 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In some embodiments, the electron transport layer may be aluminum quinolate ($Alq_3$), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), a derivative or a combination thereof, or any other material known in the art to be useful as an electron-transport material.

A hole-injection layer may include any material that can inject holes. Some examples of hole-injection materials may include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl)benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl)benzene, a polyacetylene derivative such as poly(1,2-bis-benzylthio-acetylene), a phthalocyanine metal complex derivative such as phthalocyanine copper (CuPc), a combination thereof, or any other material known in the art to be useful as a hole-injection material. In some embodiments, hole-injection materials, while still being able to transport holes, may have a hole mobility substantially less than the hole mobility of conventional hole-transport materials.

Figure 7:
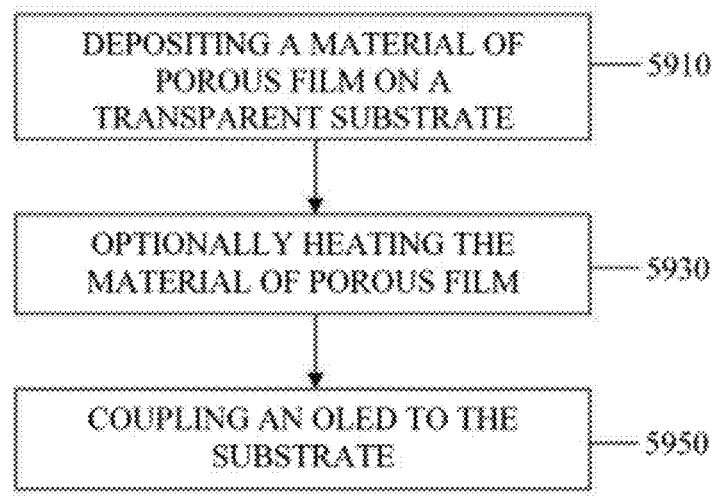
FIG. 7 is a schematic diagram related to preparation of a device described herein.

A variety of methods may be used to provide a porous film layer to a light-emitting device. FIG. 7 depicts an example of a method that may be used. The first step 5910 involves depositing a material of porous film on a transparent substrate. An optional heating step 5930 may then be carried out upon the material deposited on the transparent substrate to provide a porous film. Then an OLED is coupled to the substrate 5570 using a coupling medium in step 5950.

A coupling medium may be any material that has a similar refractive index to the glass substrate and may be capable of causing the glass substrate to be affixed to the OLED, such as by adhesion. Examples may include a refractive index matching oil or double sticky tape. In some embodiments, a glass substrate may have a refractive index of about 1.5, and a coupling medium may have a refractive index of about 1.4. This may allow light to come through the glass substrate and the coupling medium without light loss.

In some embodiments, the material of the porous film may be deposited directly on the OLED. An optional heating step may also be carried out on the deposited material to provide a porous film.

In some embodiments, the heating temperature may be sufficiently low that the performance of the OLED is not adversely affected to a degree that is unacceptable. In some embodiments, annealing (i.e., heating step) may not be necessary.

A light-emitting device may further comprise an encapsulation or protection layer to protect the porous film element from environmental damage, such as damage due to moisture, mechanical deformation, etc. For example, a protective layer may be placed in such a way as to provide a protective barrier between the porous film and the environment.

Figure 8:
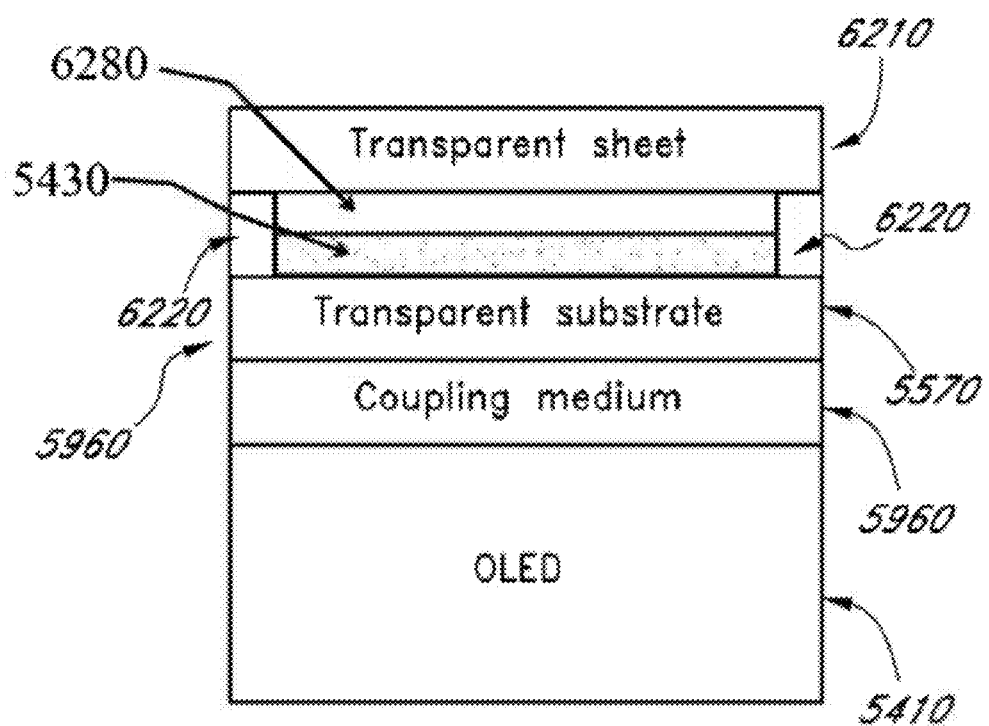
FIG. 8 is a schematic diagram of some embodiments of a device described herein.
Figure 9:
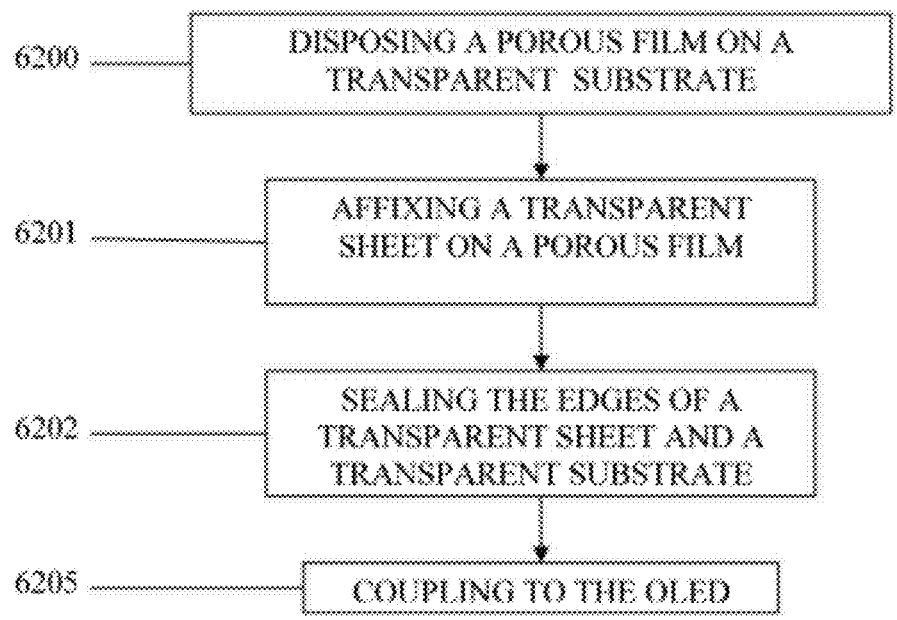
FIG. 9 is a schematic diagram related to the preparation of some embodiments of a device described herein.

While there may be many ways to encapsulate or protect a porous film, FIG. 8 is a schematic of a structure of an encapsulated device and FIG. 9 shows one method that may be used to prepare the device. In this method, step 6200 involves disposing a porous film 5430 on a transparent substrate 5570, and step 6201 involves affixing a transparent sheet 6210 over a porous film 5430. When the transparent sheet 6210 is positioned over the porous film 5430, the edges of the transparent sheet 6210 and the transparent substrate 5570 may be sealed to one another by a sealing material 6220 as shown in step 6202. The sealing material 6220 may be an epoxy resin, a UV-curable epoxy, or another cross-linkable material. Optionally, a gap 6280 may be present between the transparent sheet 6210 and the porous material 5430. A protection layer (i.e., transparent sheet) may also be coated onto the porous film 5430 without sealing the edges of the protection layer 6250 and the transparent substrate 5570. In step 6205, the encapsulated porous film may then be coupled to an OLED 5410 by a coupling medium 5960. If desired, additional layers may be included in the light-emitting device. These additional layers may include an electron injection layer (EIL), a hole-blocking layer (HBL), and/or an exciton-blocking layer (EBL).

If present, an electron injection layer may be in a variety of positions in a light-emitting device, such as any position between the cathode layer and the light emitting layer. In some embodiments, the lowest unoccupied molecular orbital (LUMO) energy level of the electron injection material(s) is high enough to prevent it from receiving an electron from the light emitting layer. In other embodiments, the energy difference between the LUMO of the electron injection material(s) and the work function of the cathode layer is small enough to allow the electron injection layer to efficiently inject electrons into the emissive layer from the cathode. A number of suitable electron injection materials are known to those skilled in the art. Examples of suitable electron injection materials may include but are not limited to, an optionally substituted compound selected from the following: LiF, CsF, Cs doped into electron transport material as described above or a derivative or a combination thereof.

If present, a hole-blocking layer may be in a variety of positions in a light-emitting device, such as any position between the cathode and the emissive layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]triazole, 2,9-dimethyl-4,7-diphenyl-1,10-phenanthroline, 1,1-bis(4-bis(4-methylphenyl)aminophenyl)-cyclohexane, etc, and combinations thereof.

If present, an exciton-blocking layer may be in a variety of positions in a light-emitting device, such as in any position between the emissive layer and the anode. In some embodiments, the band gap energy of the material(s) that comprise exciton-blocking layer may be large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate ($Alq_3$), 4,4'-bis[N-(naphthyl)-N-phenyl-amino]biphenyl (α-NPD), 4,4'-N,N'-dicarbazole-biphenyl (CBP), and bathocuproine (BCP), and any other material(s) that have a large enough band gap to substantially prevent the diffusion of excitons.

Example 1

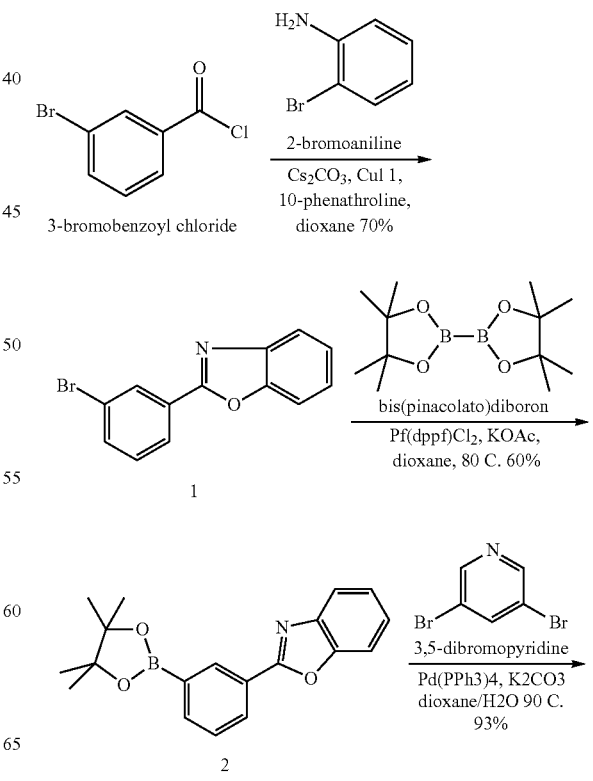

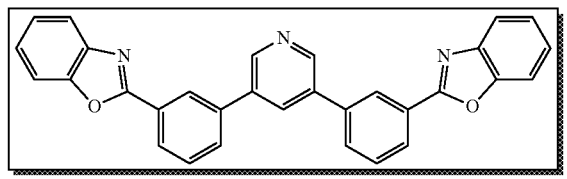

Compound-3

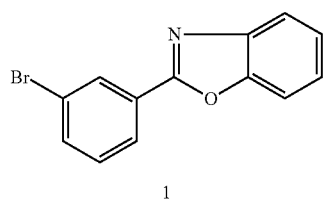

1

2-(3-bromophenyl)benzo[d]oxazole (1)

A mixture of 3-bromobenzoyl chloride (10.0 g, 45.6 mmol), 2-bromoaniline (7.91 g, 46 mmol), Cs$_2$CO$_3$ (30 g, 92 mmol), CuI (0.437 g, 2.3 mmol) and 1,10-phenanthroline (0.829 g, 4.6 mmol) in anhydrous 1,4-dioxane (110 ml) was heated at 120° C. for 8 h. After cooling to RT, the mixture was poured into ethyl acetate (300 ml), worked up with water (250 ml). The aqueous solution was extracted with dichloromethane (300 ml). The organic phase was collected, combined, and dried over Na$_2$SO$_4$. Purification by a short silica gel column (hexanes/ethyl acetate 3:1) gave a solid which was washed with hexanes to give a light yellow solid 1 (9.54 g, 76% yield).

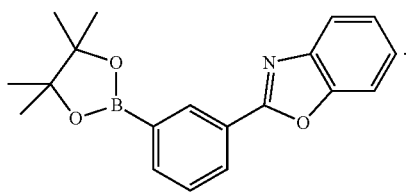

2

2-(3-(4,4,5,5-tetramethyl-1,3,2-dioxaborolan-2-yl)phenyl)benzo[d]oxazole (2)

A mixture of 2-(3-bromophenyl)benzo[d]oxazole (1) (2.4 g, 8.8 mmol), bis(pinacolato)diboron (2.29 g, 9.0 mmol), [1,1'-Bis(diphenylphosphino)ferrocene]dichloropalladium (0.27 g, 0.37 mmol), and potassium acetate (2.0 g, 9.0 mmol) in anhydrous 1,4-dioxane (50 mL) was degassed, then heated at 80° C. overnight. After cooling to RT, the mixture was poured into ethyl acetate (100 ml). After filtration, the solution was absorbed on silica gel and purified by flash chromatography (hexanes/ethyl acetate 4:1) to give a white solid 2 (2.1 g in 75% yield).

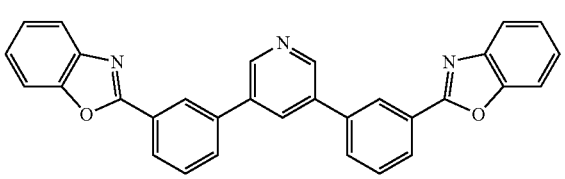

Compound-3:

A mixture of 3,5-dibromopyridine (0.38 g, 1.6 mmol), 2-(3-(4,4,5,5-tetramethyl-1,3,2-dioxaborolan-2-yl)phenyl)benzo[d]oxazole (2) (1.04 g, 3.1 mol), Pd(PPh$_3$)$_4$ (0.20 g, 0.17 mmol) and potassium carbonate (0.96 g, 7.0 mmol) in dioxane/water (40 ml/8 ml) was degassed and heated at 90° C. overnight under argon. After cooling to RT, the precipitate was filtered and washed with methanol to give a white solid 3 (0.73 g, in 95% yield).

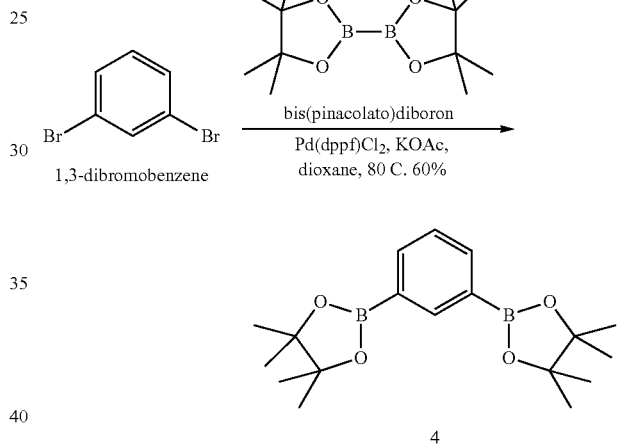

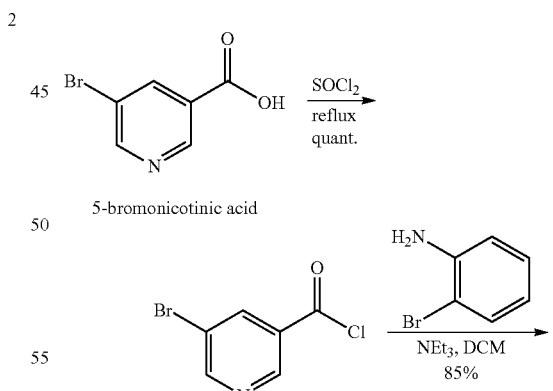

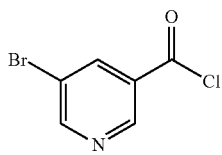

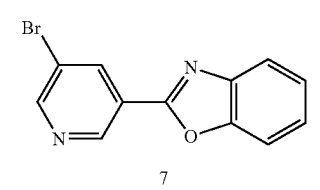

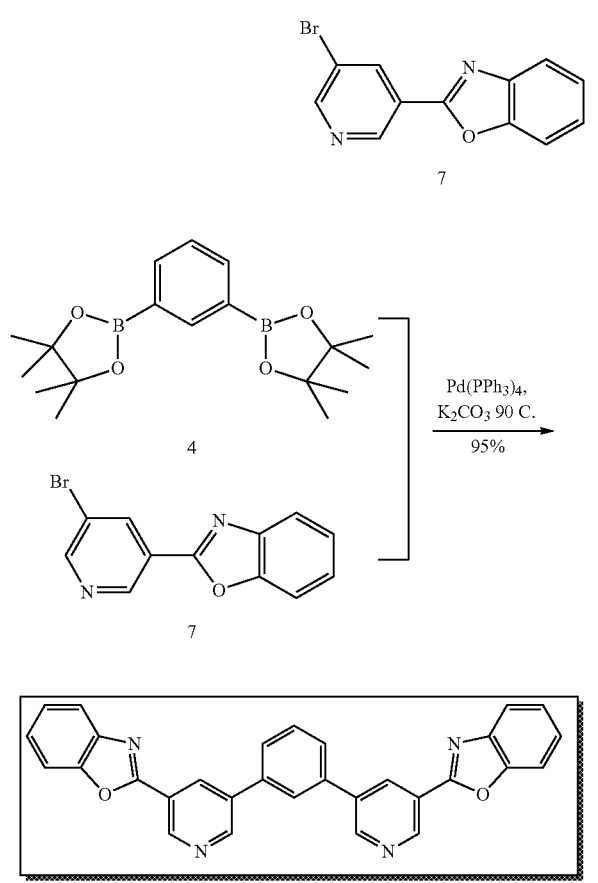

Compound-8

1,3-bis(4,4,5,5-tetramethyl-1,3,2-dioxaborolan-2-yl)benzene (4)

1,3-dibromobenzene (2.5 g, 10.6 mmol), bis(pinacolato)diboron (6.0 g, 23.5 mmol), Pd(dppf)₂Cl₂ (0.9 g, 1.2 mmol), and potassium acetate (7.1 g, 72.1 mmol) were dissolved in 50 mL of 1,4-dioxane. The reaction mixture was degassed with argon and then heated to 85° C. under argon for 18 hours. The reaction mixture was filtered and an extraction was performed in ethyl acetate. The organic phase was washed with water and brine. The extract was dried over sodium sulfate, filtered, and concentrated. The resulting residue was purified by a silica gel column with 1:9 ethyl acetate:hexanes as the eluent. The solvents were removed and the product was recrystallized from dichloromethane/methanol to yield the product as an off-white solid 4 (3.008 g, 86% yield).

5-Bromonicotinoyl chloride (5)

To a mixture of 5-bromonicotinic acid (10 g) in thionyl chloride (25 ml) was added anhydrous DMF (0.5 ml). The whole was heated to reflux for overnight. After cooled to RT, the excess thionyl chloride was removed under reduced pressure. A white solid 5 (11 g) was obtained, which was used for the next step without further purification.

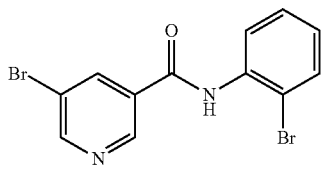

5-bromo-N-(2-bromophenyl)nicotinamide (6)

A mixture of 5-bromonicotinoyl chloride 5 (7.5 g, 33 mmol), 2-bromoaniline (5.86 g, 33 mmol) and triethylamine (14 mL, 100 mmol) in anhydrous dichloromethane (100 ml) was stirred under argon overnight. The resulting mixture was worked up with water and extracted with dichloromethane (200 mL×2). The organic phase was collected and dried over Na₂SO₄. After concentrated to 150 mL, white crystalline solid was crashed out. Filtration and washing with hexanes gave a white solid 6 (10.0 g, 85% yield).

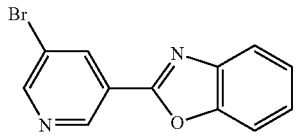

2-(5-bromopyridin-3-yl)benzo[d]oxazole (7)

A mixture of 5-bromo-N-(2-bromophenyl)nicotinamide 6 (3.44 g, 9.7 mmol), CuI (0.106 g, 0.56 mmol), Cs₂CO₃ (3.91 g, 12 mmol) and 1,10-phenanthroline (0.20 g, 1.12 mmol) in anhydrous 1,4-dioxane (50 ml) was heated at 100° C. overnight. After cooling to RT, the mixture was poured into ethyl acetate (200 ml), then washed with water. The aqueous phase was extracted with ethyl acetate (200 ml×2), and the organic phase was collected and dried over Na₂SO₄, purified by flash chromatography (silica gel, hexanes/ethyl acetate 3:1) to give a light yellow solid 7 (2.0 g, 75% yield).

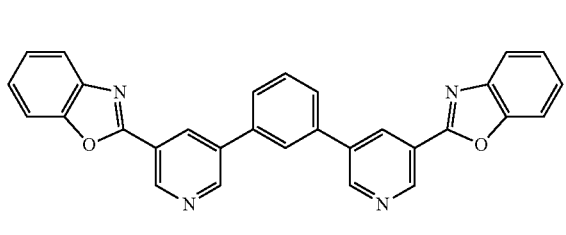

8

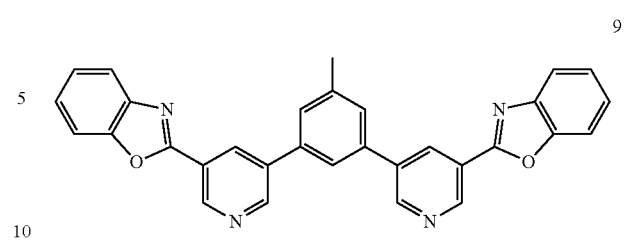

9

Compound-8:

A mixture of 1,3-bis(4,4,5,5-tetramethyl-1,3,2-dioxaborolan-2-yl)benzene 4 (0.63 g, 1.92 mmol), 2-(5-bromopyridin-3-yl)benzo[d]oxazole 7 (1.05 g, 3.83 mmol), Pd(PPh$_3$)$_4$ Compound 9:

Compound 9 was prepared using a similar procedure as Compound 8, except that 1,3-dibromo-5-methylbenzene was used in place of 1,3-dibromobenzene.

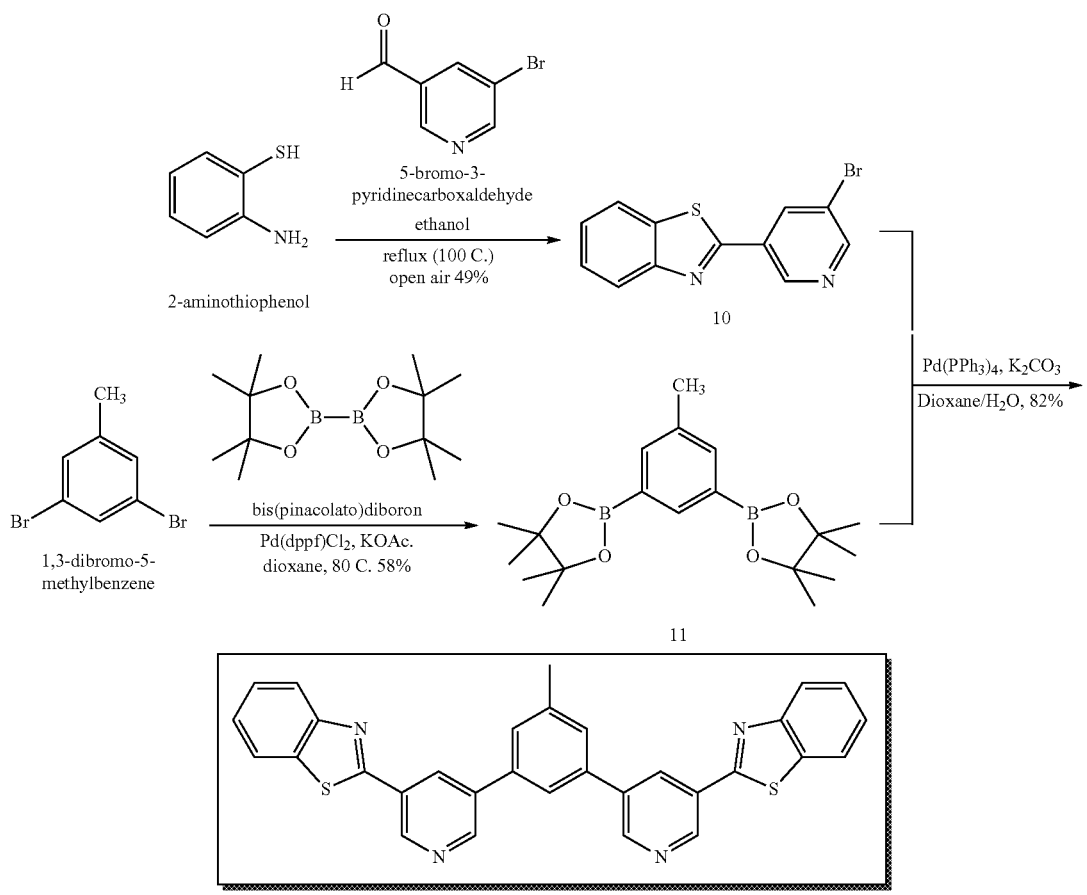

(0.219 g, 0.19 mmol) and potassium carbonate (1.1 g, 8 mmol) in dioxane/water (30 ml/6 ml) was degassed and heated at 85° C. overnight under argon. After cooling to RT, the precipitate was filtered and washed with methanol (300 ml×3) and dried under vacuum to give a white solid 8 (0.88 g, 98% yield).

2-(5-bromopyridin-3-yl)benzo[d]thiazole (10)

To a mixture of 2-aminothiophenol (500 mg, 3.99 mmol) and 5-bromo-3-pyridinecarboxaldehyde (743 mg, 3.99 mmol) was added ethanol (10 mL). The mixture was then heated to reflux (100° C.) overnight under ambient air. After cooling, the mixture was dried under vacuum then redissolved in methylene chloride (100 ml). Solution was washed with water (100 ml) and brine (50 ml), and dried over sodium sulfate. The crude material was run through a plug of silica (16% ethyl acetate in hexanes), and precipitated from methanol to give 564 mg of the material 10 in 49% yield.

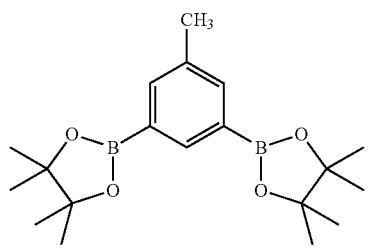

2,2'-(5-methyl-1,3-phenylene)bis(4,4,5,5-tetramethyl-1,3,2-dioxaborolane) (11)

1,3-dibromo-5-methylbenzene (5.0 g, 20.0 mmol), bis(pinacolato)diboron (11.3 g, 44.4 mmol), Pd(dppf)Cl$_2$ (1.6 g, 2.2 mmol), and potassium acetate (13.3 g, 136.0 mmol) were dissolved in 75 ml of 1,4-dioxane. The reaction mixture was degassed with argon and then heated to 85° C. under argon for 18 hours. The reaction mixture was filtered and an extraction was performed in ethyl acetate. The organic phase was washed with water and brine, then dried over magnesium sulfate, filtered, and concentrated. The resulting residue was purified by a silica gel column with 1:4 ethyl acetate:hexanes as the eluent to yield the product as an off-white solid (0.399 g, 58% yield).

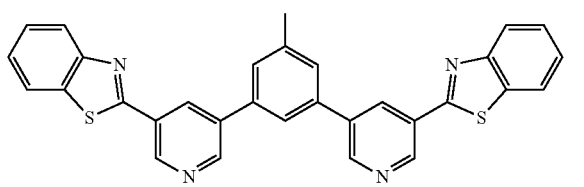

Compound-12:

A mixture of 2,2'-(5-methyl-1,3-phenylene)bis(4,4,5,5-tetramethyl-1,3,2-dioxaborolane) 11 (0.747 g, 2.17 mmol), 2-(5-bromopyridin-3-yl)benzo[d]thiazole 10 (1.39 g, 4.77 mmol), Pd(PPh$_3$)$_4$ (0.165 g, 0.143 mmol) and potassium carbonate (1.81 g, 17.0 mmol) in THF/water (30 ml/17 ml) was degassed and heated at reflux (85° C.) overnight under argon. After cooling to RT, the mixture was filtered and the solid was washed with water, methanol and THF. The solid was collected and the filtrate was added to water (150 ml) and extracted with dichloromethane (150 ml×2). The organic solution was dried over Na$_2$SO$_4$ and loaded on silica gel, purified by flash column using hexanes/acetone (4:1 to 3:1). The desired fraction was collected and combined with the solid from the first filtration. The solid was washed with hot dichloromethane, filtered and washed with methanol to afford 0.91 g product 12 in 82% yield.

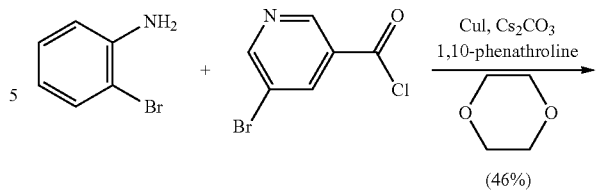

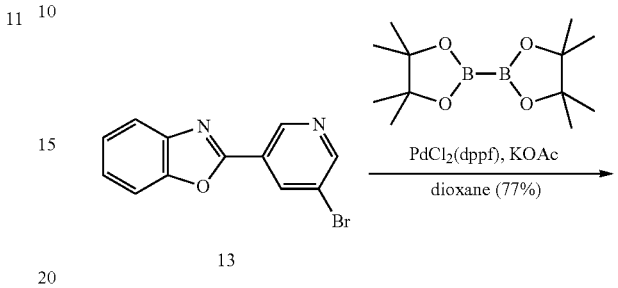

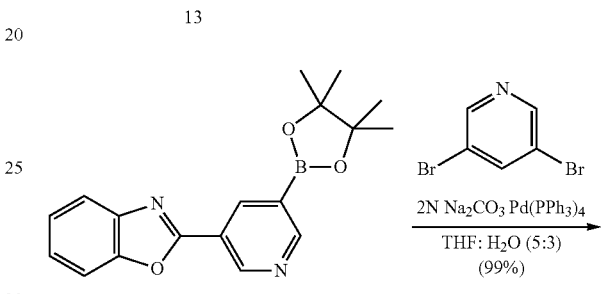

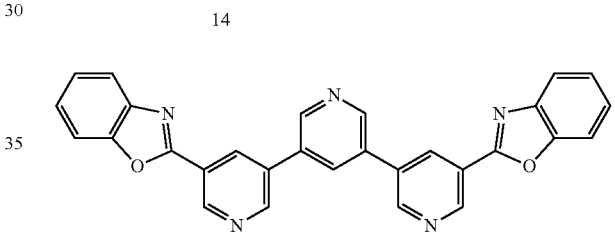

Compound-15

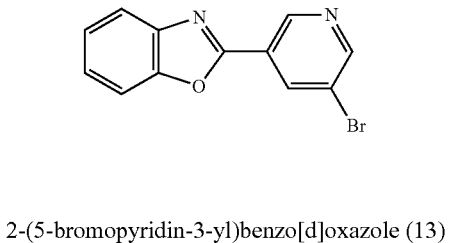

2-(5-bromopyridin-3-yl)benzo[d]oxazole (13)

A mixture of 5-bromonicotinoyl chloride (13.46 g, 61.04 mmol), 2-bromoaniline (10.00 g, 58.13 mmol), Cs$_2$CO$_3$ (37.88 g, 116.3 mmol), CuI (0.554 g, 2.907 mmol), 1,10-phenanthroline (1.048 g, 5.813 mmol) and anhydrous 1,4-dioxane (110 mL) was degassed with argon for 1 h while stirring. The reaction mixture was then maintained under argon at 120° C. while stirring until TLC (SiO$_2$, 1:1 hexanes-dichloromethane) confirmed consumption of the starting material (48 h). Upon cooling to RT, dichloromethane (ca. 200 mL) was added to the reaction, the mixture filtered, the filtrant washed copiously with dichloromethane (ca. 200 mL) and ethyl acetate (ca. 200 mL) and the filtrate concentrated in vacuo. Purification of the crude product via flash chromatography (SiO$_2$, 100% dichloromethane to 29:1-dichloromethane:acetone) afforded 2-(5-bromopyridin-3-yl)benzo[d]oxazole (7.32 g, 46%) as a light brown crystalline solid.

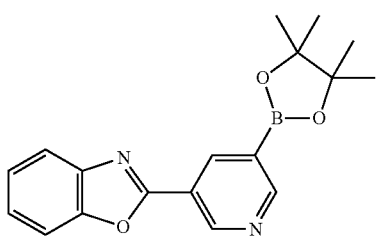 [SMILES: CC1(C)OB(c2cncc(-c3nc4ccccc4o3)c2)OC1(C)C]

2-(5-bromopyridin-3-yl)benzo[d]oxazole (14)

A mixture of 2-(5-bromopyridin-3-yl)benzo[d]oxazole (7.119 g, 25.88 mmol), bis(pinacolato)diboron (7.229 g, 28.47 mmol), [1,1'-Bis(diphenylphosphino)ferrocene]dichloropalladium (0.947 g, 1.294 mmol), potassium acetate (7.619 g, 77.63 mmol) and anhydrous 1,4-dioxane (150 mL) was maintained under argon at 100° C. while stirring until TLC (SiO$_2$, 9:1 dichloromethane:acetone) confirmed consumption of the starting material (3 days). Upon cooling to RT, dichloromethane (ca. 300 mL) was added to the reaction, the mixture filtered and the filtrant washed with dichloromethane (ca. 100 mL). The filtrate was then washed with sat. NaHCO$_3$, H$_2$O and brine, dried over MgSO$_4$, filter and concentrated in vacuo. The crude product was purified by filtration from hot hexanes and the resulting filtrate concentrated to yield 2-(5-bromopyridin-3-yl)benzo[d]oxazole (6.423 g, 77%) as an orangish-brown solid via recrystallization.

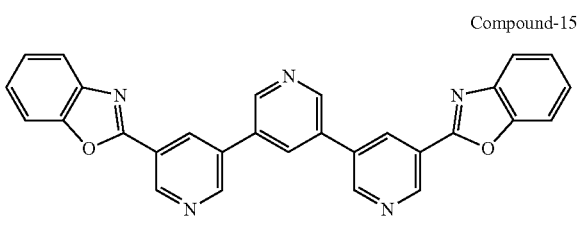 [SMILES: c1ccc2oc(-c3cncc(-c4cncc(-c5cncc(-c6nc7ccccc7o6)c5)c4)c3)nc2c1]

Compound-15

5,5''-bis(benzo[d]oxazol-2-yl)-3,3':5',3''-terpyridine (Compound-15)

A mixture of 2-(5-bromopyridin-3-yl)benzo[d]oxazole (2.000 g, 6.208 mmol), 3,5-dibromopyridine (0.7003 g, 2.956 mmol), tetrakis(triphenylphosphine)palladium(0) (0.205 g, 0.177 mmol), Na$_2$CO$_3$ (3.18 g, 30.0 mmol), H$_2$O (15 mL) and THF (25 mL) was degassed with argon for 27 min while stirring. The reaction mixture was then maintained under argon at 85° C. for 16 h. Upon cooling to RT, the reaction mixture was filtered and the filtrant washed copiously with H$_2$O and methanol to provide Compound-15 (1.36 g, 99%) as an off-white solid.

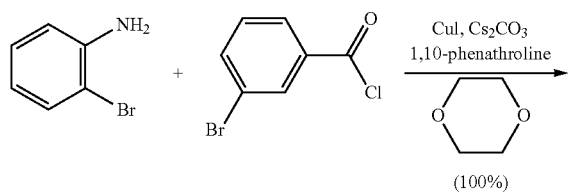

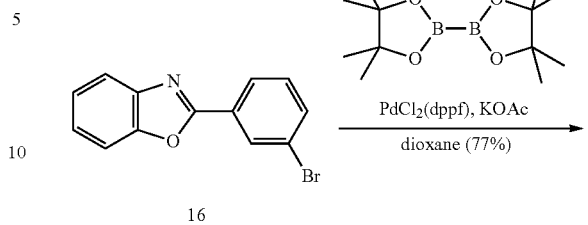

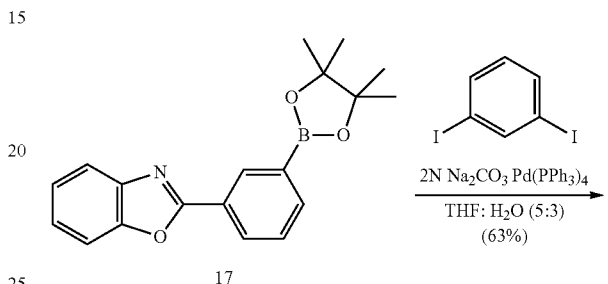

Compound-18

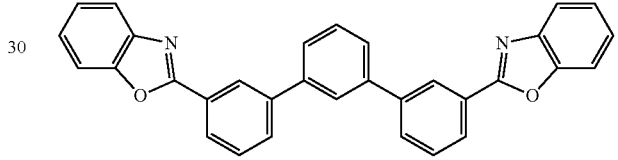

(16)

2-(3-bromophenyl)benzo[d]oxazole (16)

A mixture of 3-bromobenzoyl chloride (6.005 g, 27.36 mmol), 2-bromoaniline (4.707 g, 27.36 mmol), Cs$_2$CO$_3$ (17.83 g, 54.73 mmol), CuI (0.261 g, 1.37 mmol), 1,10-phenanthroline (0.493 g, 2.74 mmol) and anhydrous 1,4-dioxane (50 mL) was degassed with argon at 40° C. for 30 min while stirring. The reaction mixture was then maintained under argon at 120° C. while stirring until TLC (SiO$_2$, 4:1 hexanes-ethyl acetate) confirmed consumption of the starting material (24 h). Upon cooling to RT, the mixture was filtered and the filtrant washed copiously with ethyl acetate (ca. 350 mL). The filtrate was then washed with sat. NaHCO$_3$, H$_2$O and brine, dried over MgSO$_4$, filter and concentrated in vacuo. Purification of the crude product via flash chromatography (SiO$_2$, 4:1-hexanes:ethyl acetate) afforded 2-(3-bromophenyl)benzo[d]oxazole (7.50 g, 100%) as an off-white solid.

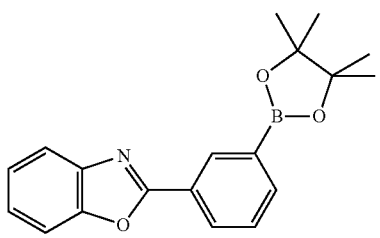

(17)

2-(3-(4,4,5,5-tetramethyl-1,3,2-dioxaborolan-2-yl)phenyl)benzo[d]oxazole (17)

A mixture of 2-(3-bromophenyl)benzo[d]oxazole (7.500 g, 27.36 mmol), bis(pinacolato)diboron (7.296 g, 28.73 mmol), [1,1'-Bis(diphenylphosphino)ferrocene]dichloropalladium (1.001 g, 1.368 mmol), potassium acetate (6.176 g, 62.93 mmol) and anhydrous 1,4-dioxane (71 mL) was degassed with argon at 40° C. for 37 min while stirring. The reaction mixture was then maintained under argon at 100° C. while stirring until TLC (SiO$_2$, 2:1 hexanes-dichloromethane) confirmed consumption of the starting material (21 h). Upon cooling to RT, the mixture was filtered and the filtrate washed copiously with ethyl acetate (ca. 700 mL). The filtrate was then washed with sat. NaHCO$_3$, H$_2$O and brine, dried over MgSO$_4$, filter and concentrated in vacuo. Purification of the crude product via flash chromatography (SiO$_2$, 9:1-dichloromethane:hexanes to 19:1-dichloromethane:acetone) afforded 2-(3-(4,4,5,5-tetramethyl-1,3,2-dioxaborolan-2-yl)phenyl)benzo[d]oxazole (6.76 g, 77%) as an off-white solid.

Compound-18

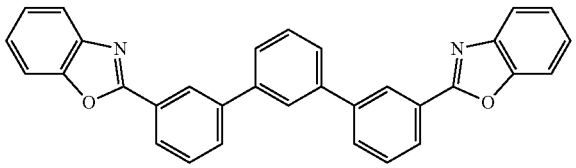

3,3''-bis(benzo[d]oxazol-2-yl)-1,1':3',1''-terphenyl (Compound-18)

A mixture of 2-(3-(4,4,5,5-tetramethyl-1,3,2-dioxaborolan-2-yl)phenyl)benzo[d]oxazole (2.25 g, 7.01 mmol), 1,3-diiodobenzene (1.101 g, 3.337 mmol), tetrakis(triphenylphosphine)palladium(0) (0.193 g, 0.167 mmol), Na$_2$CO$_3$ (2.555 g, 24.11 mmol), H$_2$O (24 mL) and THF (40 mL) was degassed with argon for 33 min while stirring. The reaction mixture was then maintained under argon at 80° C. while stirring until TLC (SiO$_2$, 9:1 hexanes-acetone) confirmed consumption of the starting material (22 h). Upon completion, the reaction was cooled to RT and poured over dichloromethane (ca. 350 mL). The resulting mixture was then filtered, the filtrate washed with sat. NaHCO$_3$, H$_2$O and brine, dried over MgSO$_4$, filter and concentrated in vacuo. Purification of the crude product via flash chromatography (SiO$_2$, 19:1-dichloromethane:hexanes to 100% dichloromethane) yielded compound-18 (0.98 g, 63%) as a light yellow solid.

Device Examples

I-V-L characteristics were taken with a Keithley 2400 SourceMeter and Newport 2832-C power meter and 818 UV detector.

Control Example 1

OLED A (Device A) Preparation

Figure 10:
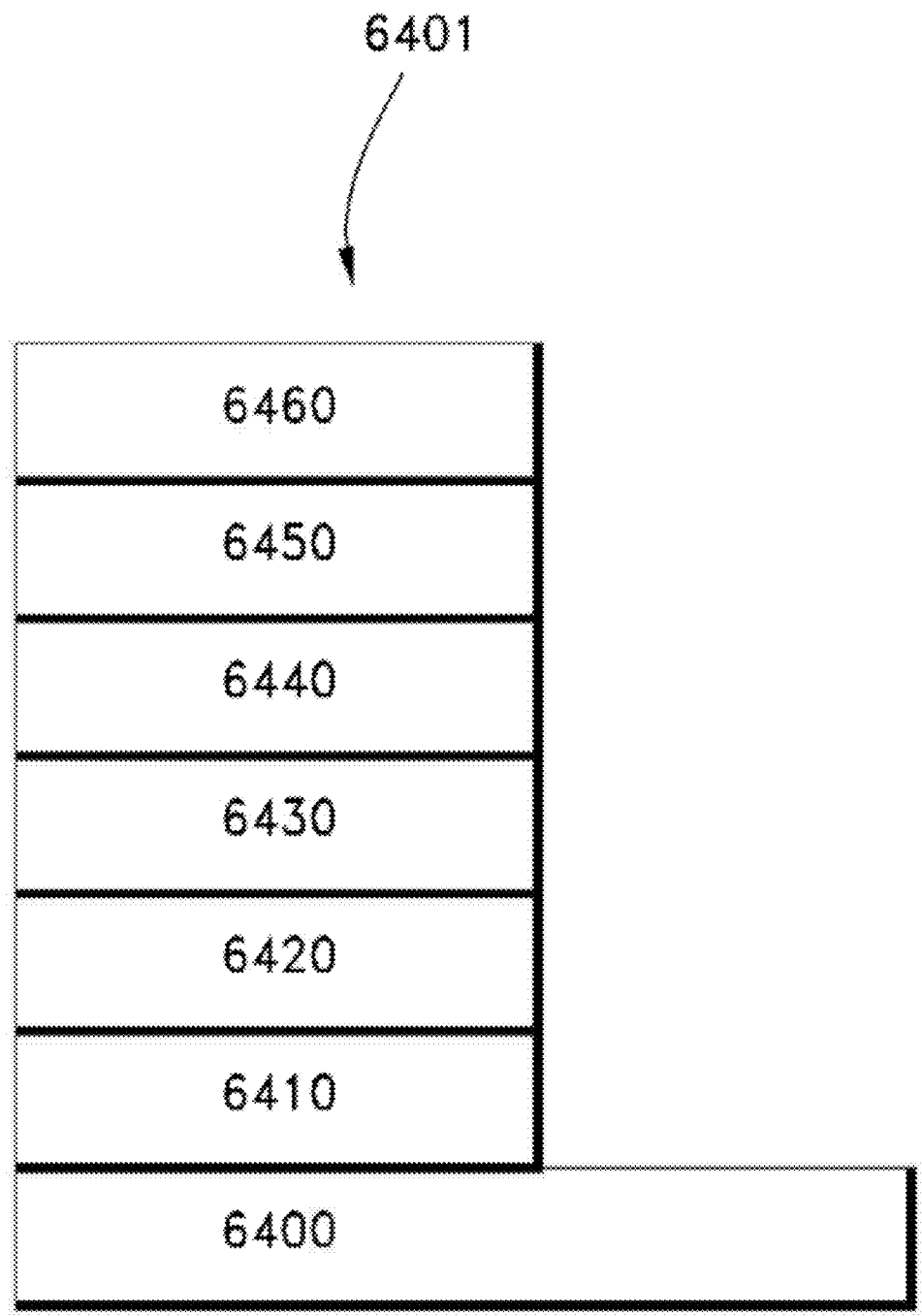
FIG. 10 is a schematic diagram of some embodiments of a device described herein.

OLED A 6401 was prepared according to the schematic shown in FIG. 10. OLED A 6401 included a cathode 6460 that was disposed on an electron-transport layer 6450, that was disposed on emissive layer 6440, that was disposed on a hole-transport layer 6430, that was disposed on a hole-injection layer 6420, that was disposed on an anode 6410, that was disposed on a transparent substrate 6400.

Although the materials may be interchangeable, in OLED A the cathode 6460 was LiF/Al, the electron-transport layer 6450 was TPBI, the emissive layer 6440 comprised about 5% PO-01 as emitter and Compound-13 as a host, the hole-transport layer 6430 was α-NPD, the hole-injection layer 6420 was PEDOT, the anode 6410 was ITO, and the transparent substrate 6400 was glass.

OLED A was prepared by the following procedure. The PEDOT hole injection layer was spin-coated on top of a pre-cleaned ITO/glass, followed by vacuum deposition of the 30 nm-thick α-NPD hole-transport layer at a deposition rate of about 1 Å/s. The emissive layer was added by co-deposition of yellow emitter PO-01 and host Compound-13 at a deposition rate of about 0.05 and about 1 Å/s, respectively, to form an emissive layer having a thickness of about 30 nm. Then TPBI was deposited at about 1 Å/s to a thickness of about 30 nm. LiF was deposited on top of ETL at 0.1 Å/s deposition rate to a thickness of about 1 nm, followed by the deposition of Al at 2 Å/s rate to a thickness of about 100 nm. The base vacuum of the chamber was about 3×10$^{-7}$ torr.

Comparative Example 2

Figure 11:
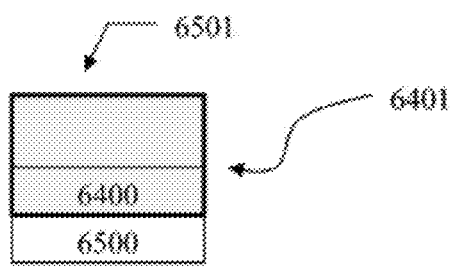
FIG. 11 is a schematic diagram of some embodiments of a device described herein.

Device B 6501 was prepared according to the schematic shown in FIG. 11. A layer of α-NPD 6500 having a thickness of 50 nm was coated onto the bottom surface of the transparent substrate 6400 of OLED A 6401. The α-NPD layer 6500 was characterized by a smooth morphology.

Device B was prepared by the same procedure as Device A except that a 50-nm thickness α-NPD layer was deposited on the outer surface of the glass substrate at a deposition rate of about 2 Å/s under a vacuum of about 4×10$^{-7}$ torr.

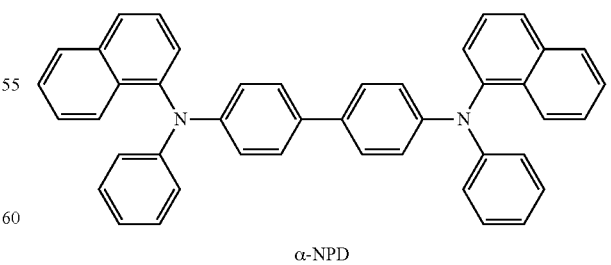

α-NPD

Figure 12:
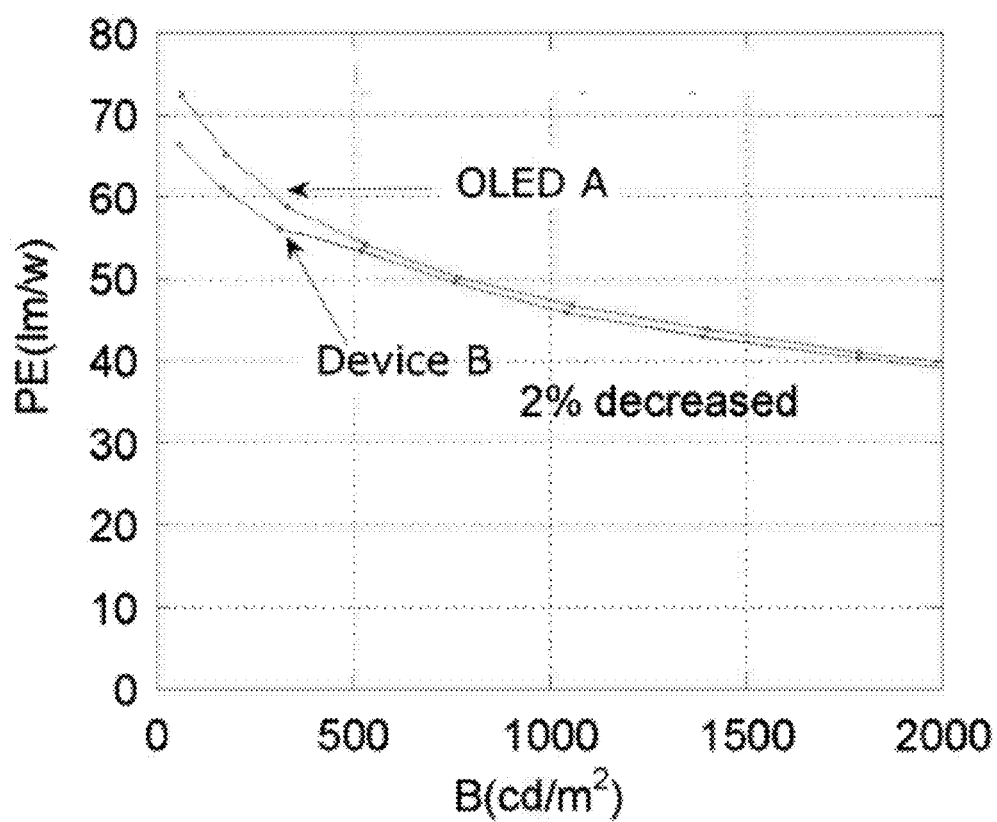
FIG. 12 is a plot of power efficiency as a function of luminance for some embodiments of devices described herein.

FIG. 12 is a plot of the power efficiency as a function of luminance (B) for OLED A as compared to Device B. The plot shows that Device B has about a 2% decrease in power efficiency as compared to OLED A over the luminance range obtained. Thus, a smooth layer of α-NPD did not appear to significantly improve device efficiency.

Comparative Example 3

Figure 13:
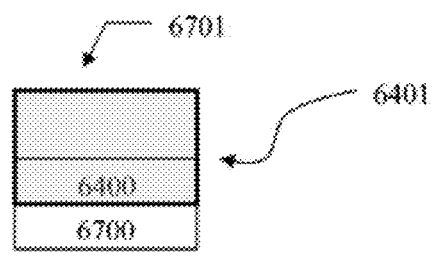
FIG. 13 is a schematic diagram of some embodiments a device described herein.
Figure 14:
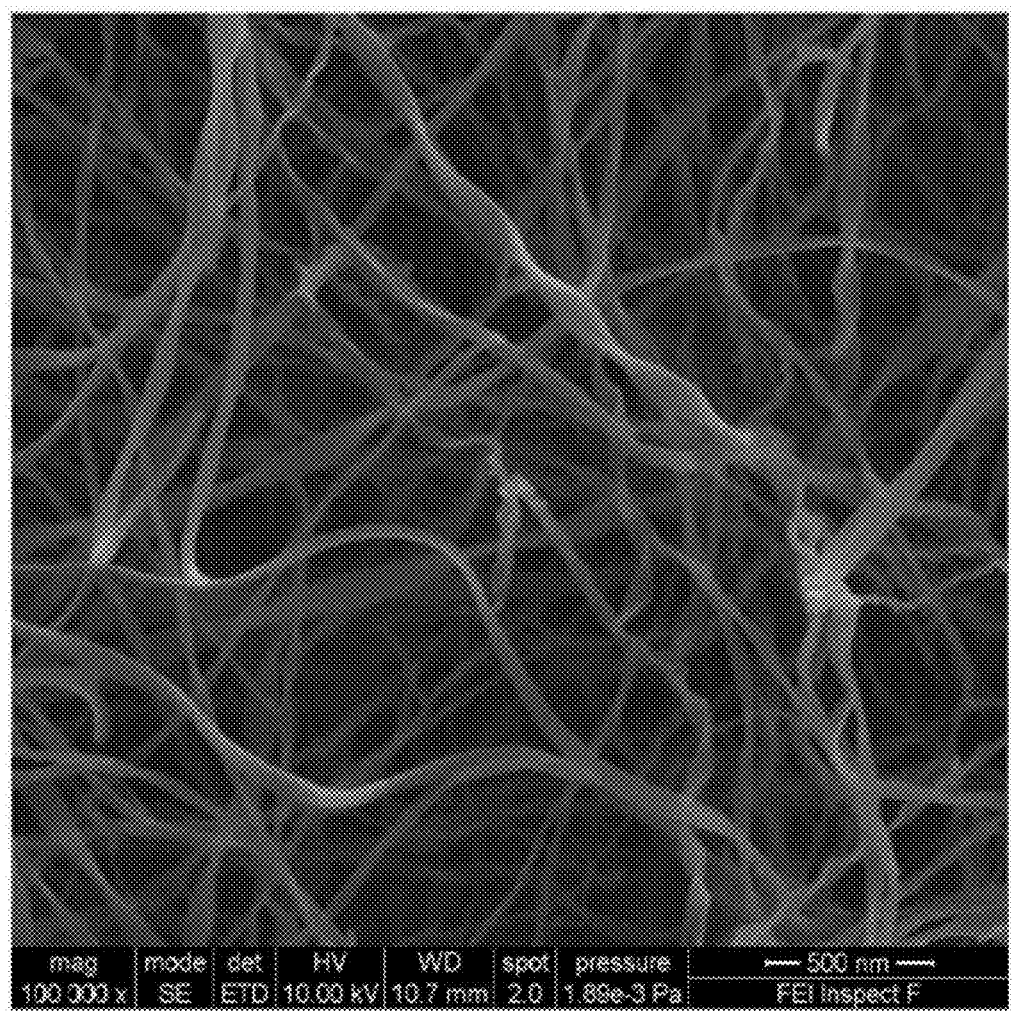
FIG. 14 depicts an SEM image of a surface a porous film of the device of FIG. 15.

Device C 6701 was prepared according to the schematic shown in FIG. 13. A layer of COMPOUND-12 6700 having a thickness of about 50 nm was coated onto the bottom surface of transparent substrate 6400 of OLED A 6401. An SEM of the layer 6700 of COMPOUND-12, depicted in FIG. 14 was characterized by a regular nanostructure that was not highly porous.

Device C was prepared by the same procedure as Device A, except that a 600 nm-thick layer of COMPOUND-12 was deposited on the bottom of the outer-face of the glass substrate at a deposition rate of about 2 Å/s under a vacuum of about $4\times10^{-7}$ torr.

Figure 15:
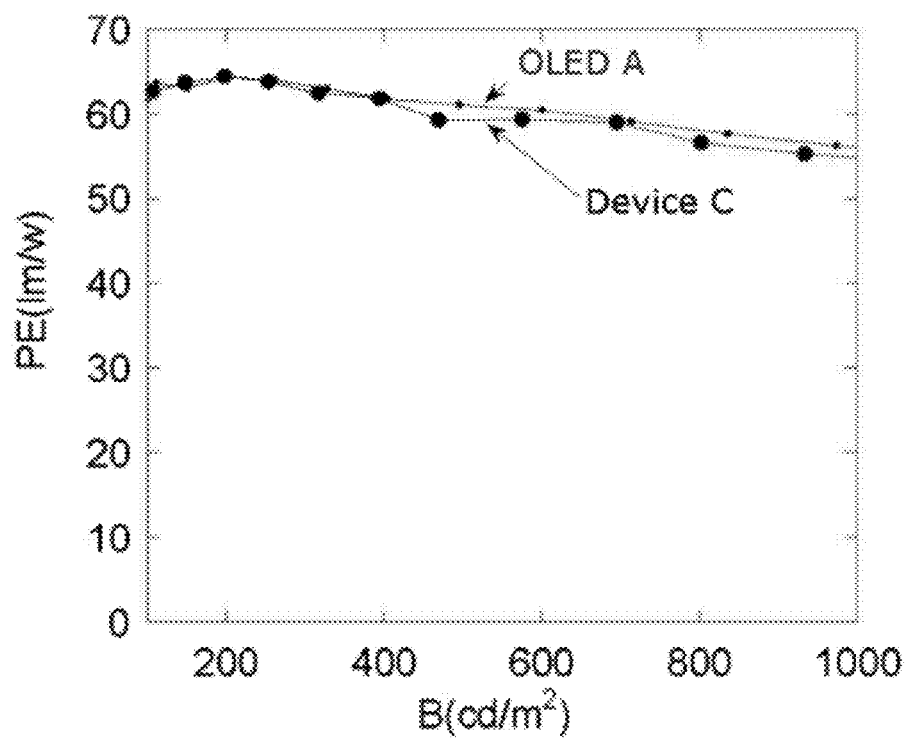
FIG. 15 is a plot of power efficiency as a function of luminance for some embodiments of devices described herein.

FIG. 15 is a plot of the power efficiency as a function of luminance (B) for OLED A as compared to Device C. The plot shows that Device C has a similar power efficiency to OLED A over the luminance range obtained. Thus, a regular nanostructure of COMPOUND-12 did not appear to improve device efficiency.

Device Example 1

Figure 16:
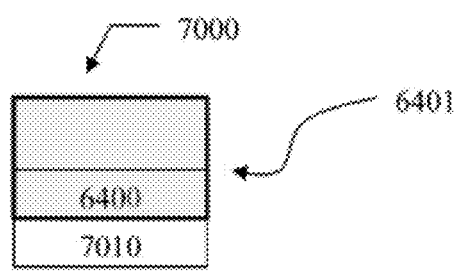
FIG. 16 is a schematic diagram of some embodiments of a device described herein.
Figure 17:
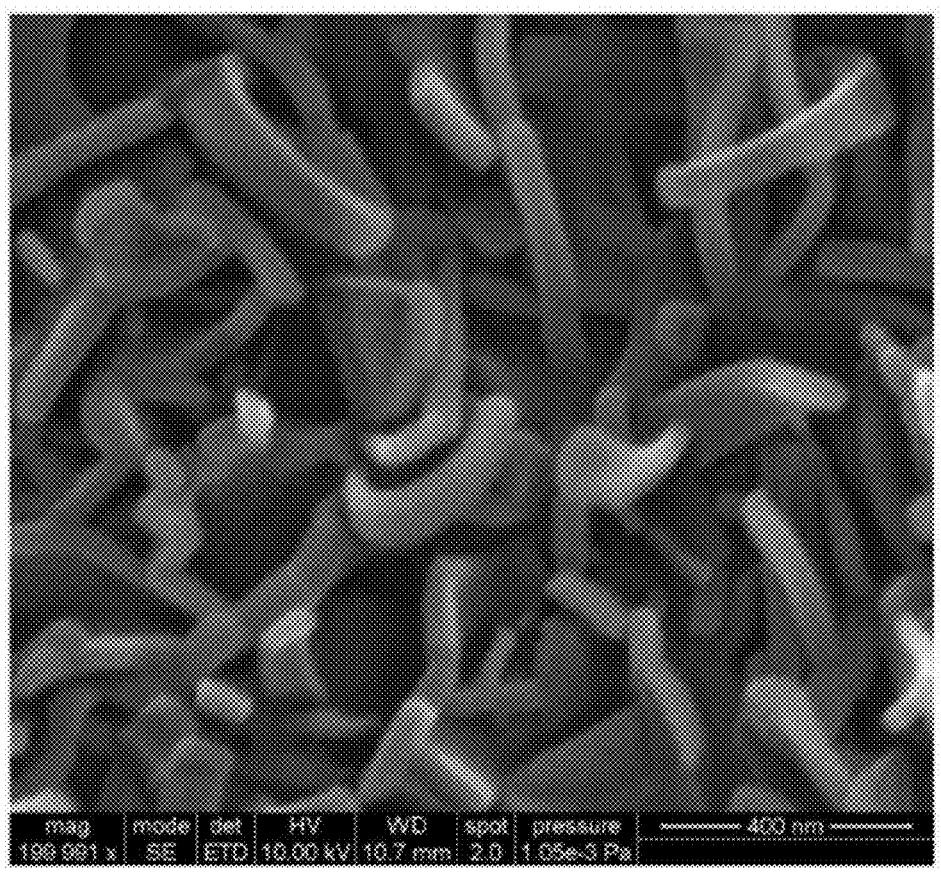
FIG. 17 depicts an SEM image of a surface of an embodiment of a porous film.

Device D 7000 was prepared according to the schematic shown in FIG. 16. A layer 7010 of COMPOUND-3 having a thickness of 3 μm was coated onto the bottom surface of transparent substrate 6400 of OLED A 6401. An SEM of the layer 7010 of COMPOUND-3 is depicted in FIG. 17 and described above.

Device D was prepared by the same procedure as Device A, except that a 600 nm-thick layer of COMPOUND-3 was deposited on the outer surface of the glass substrate. The thickness was determined by a thickness sensor installed near the deposition source that records deposition rate. The thickness obtained by the thickness sensor relies upon the assumption that the film is dense. The material was deposited at a rate that corresponded to about of 2 Å/s of dense material under a vacuum of about $4\times10^{-7}$ torr. SEM and thickness measurements showed that the deposited COMPOUND-3 layer is highly porous, and has a thickness of about 3 μm, which is about 5 times the thickness of a nonporous film.

Figure 18:
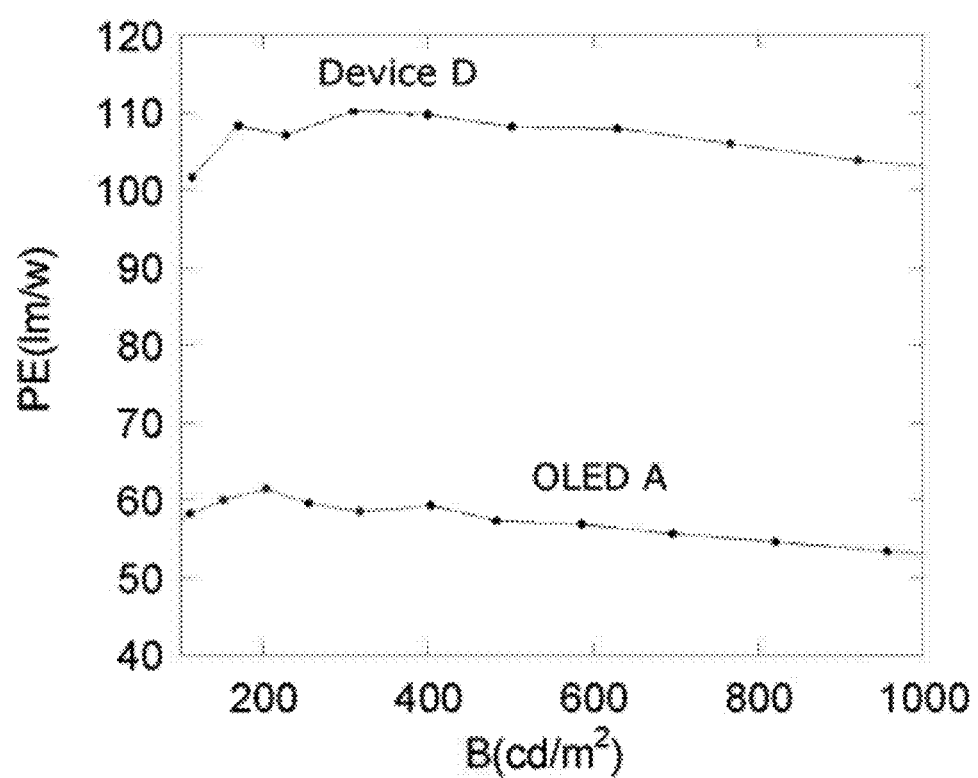
FIG. 18 is a plot of power efficiency as a function of luminance for some embodiments of devices described herein.

FIG. 18 is a plot of the power efficiency as a function of luminance (B) for OLED A as compared to Device D. Over the entire range, the efficiency of Device D was nearly twice as high as OLED A. Thus, in this example, a porous film comprising a plurality of irregularly arranged nanoprotrusions or nanoparticles provided a substantial improvement in device efficiency.

Device Example 2

Figure 19:
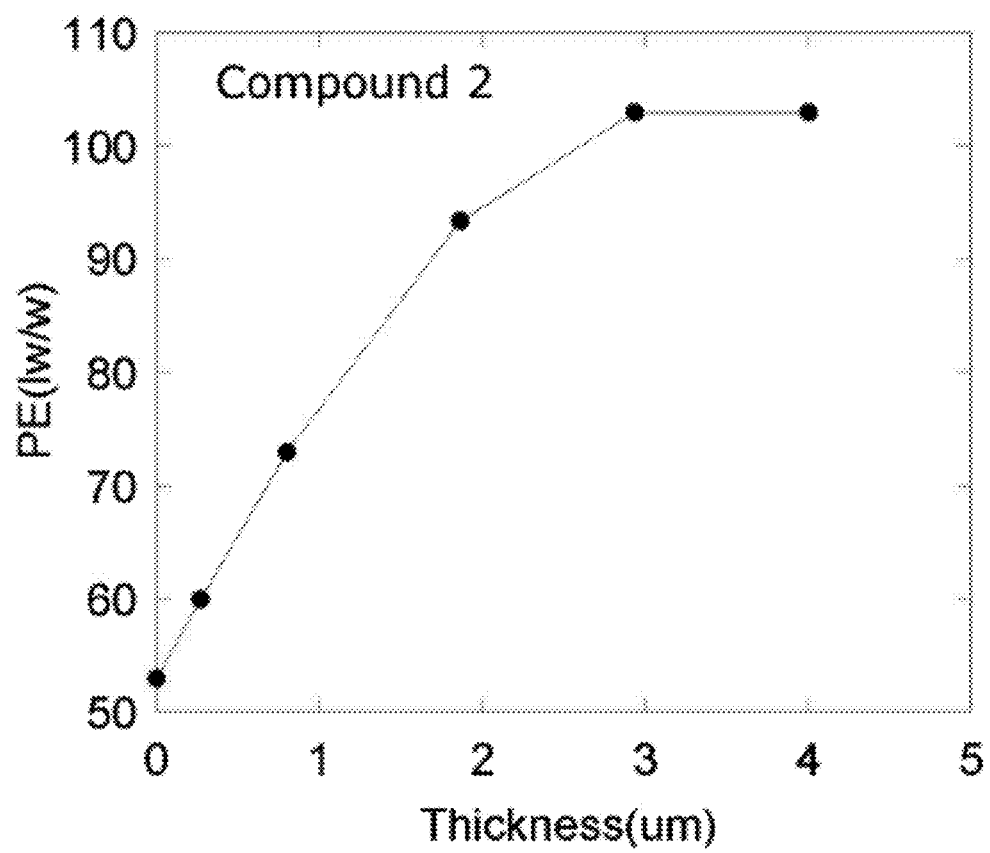
FIG. 19 is a plot of power efficiency as a function of thickness for a porous film comprising a compound described herein.

The power efficiency of a device similar to Device D was obtained with varying thickness of the COMPOUND-3 layer. FIG. 19 is a plot of the power efficiency at 1000 cd/m2 over a range of thickness of the COMPOUND-3 layer. FIG. 19 shows that PE efficiency is increased by a factor of about 1.94 at a thickness of about 3 μm or higher.

Figure 20:
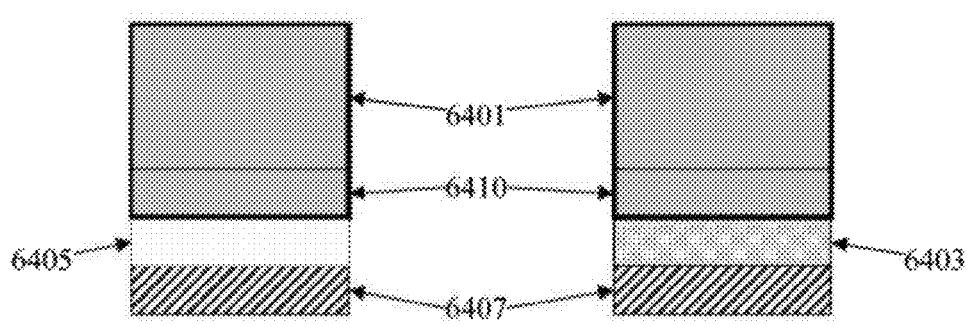
FIG. 20 is a schematic diagram of a method used to determine trapping in some embodiments of a transparent substrate.

The light extraction efficiency from the transparent substrate by the porous film was determined by the following method. The experimental setup is depicted in FIG. 20. The power efficiency of OLED A 6401 was obtained with only air 6405 between the glass substrate 6410 of the OLED device A and the surface of the light-detection sensor 6407 (Si photo diode), as shown in the left side of FIG. 20. Some light emitted from the emissive layer of the OLED will remained trapped inside the glass substrate (Glass-mode) due to the mismatch of refractive index of glass (n=1.5) and air (n=1).

OLED A was then immersed in an oil 6403 with an index of refraction of about 1.5, which is the same as the index of refraction of the transparent substrate. The oil 6403 filled substantially the entire gap between the device 6401 and the light detection sensor 6407 (Si-photo diode), so all the light trapped within the glass passes through the glass-oil interface. Thus, the Si-photo diode detector 6407 receives the amount of light it would in the ideal case of 100% light extraction.

Figure 21:
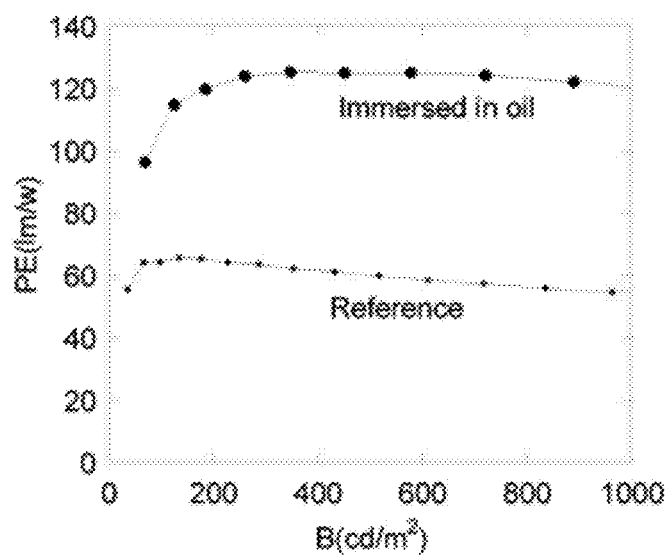
FIG. 21 is a plot of power efficiency as a function of luminance for some embodiments of devices described herein.

FIG. 21 is a plot of the efficiency of OLED A immersed in oil and obtained directly without immersion (Reference). The power efficiency of the immersed device is about twice the power efficiency of the device without the immersion (e.g. 2.18 times at 1000 cd/m²). Assuming that all of the power efficiency of the immersed device represents the 100% light extraction from the transparent substrate, Device D has a light extraction efficiency of about 89% (e.g. 1.94/2.18=0.89).

Figure 22:
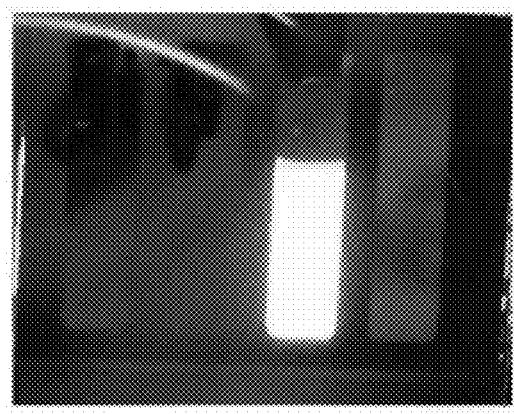
FIG. 22 is a photograph of some embodiments of the devices described herein.
Figure 23:
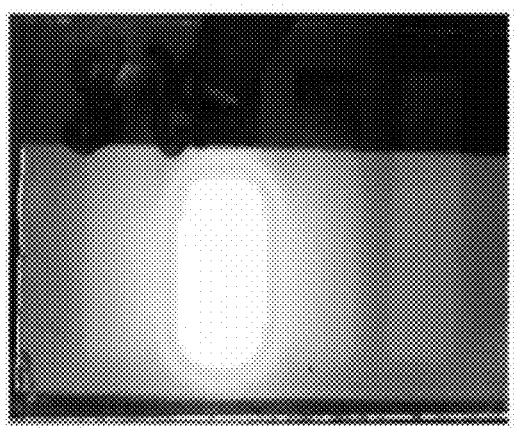
FIG. 23 is a photograph of some embodiments of the devices described herein.

FIG. 22 is a photograph of OLED A, illuminated. FIG. 23 is a photograph of Device D illuminated.

Device Example 3

Figure 24:
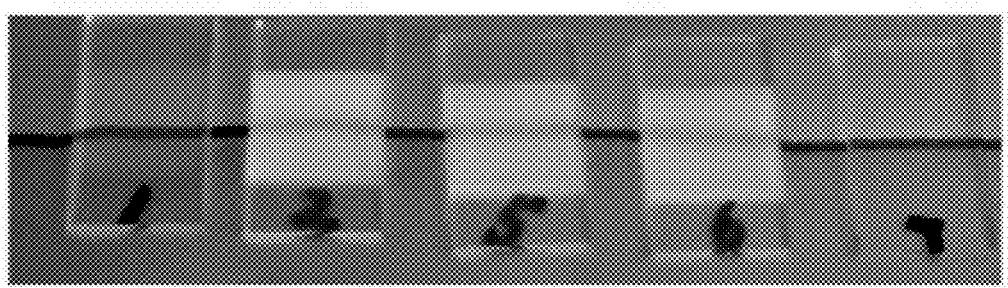
FIG. 24 is a photograph of some embodiments of the porous films described herein.
Figure 25:
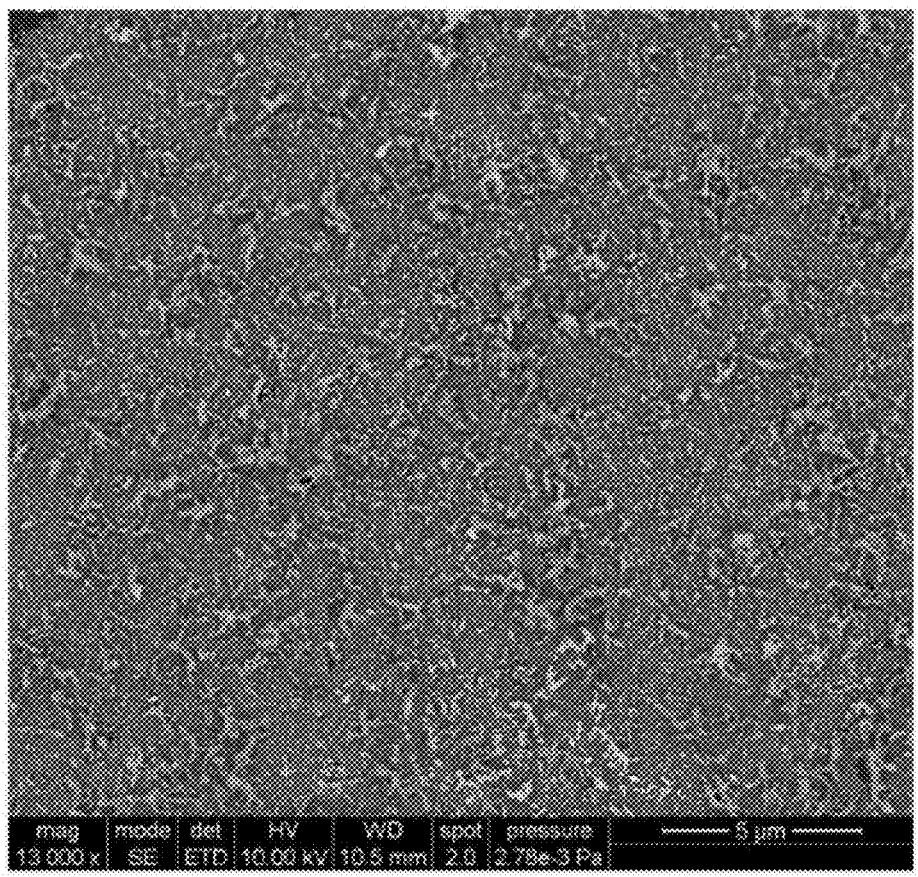
FIG. 25 depicts an SEM image of a surface of an embodiment of a porous film.

COMPOUND-8 was deposited on a glass substrate. A photograph of the film on the substrate is indicated as slide 1 in FIG. 24. An SEM of this film is depicted in FIG. 25.

Figure 26:
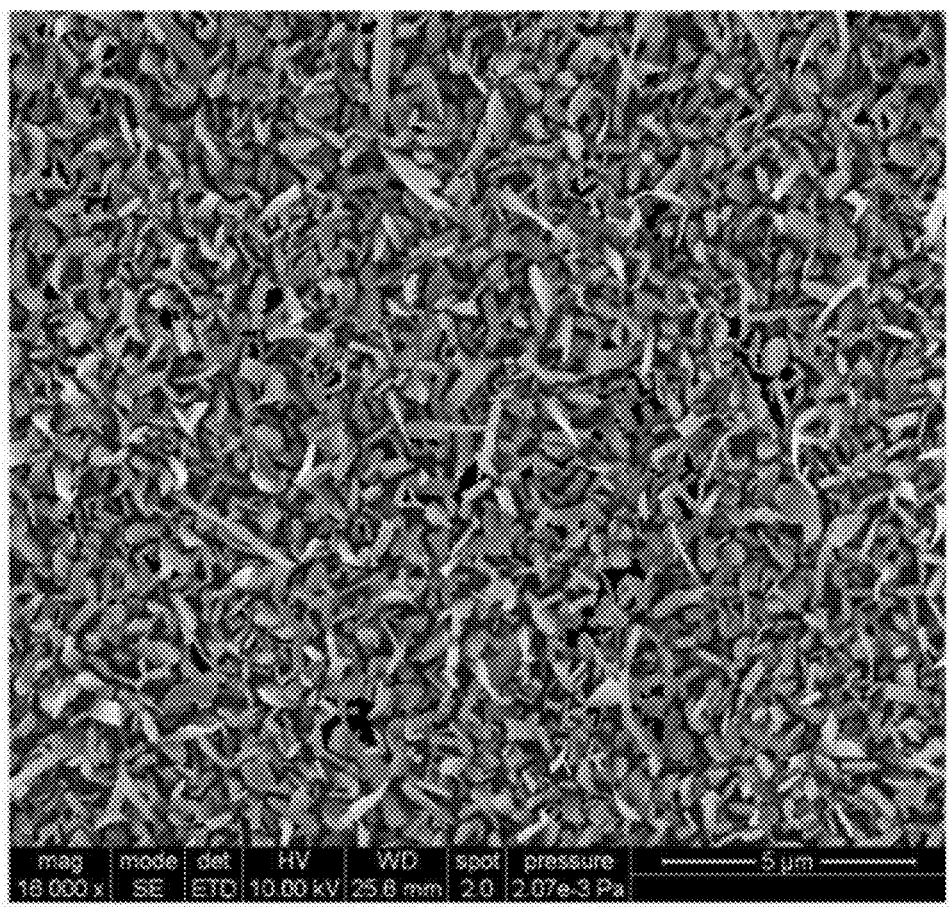
FIG. 26 depicts an SEM image of a surface of an embodiment of a porous film.

COMPOUND-8 was also deposited on a glass substrate and then heated at about 200° C. for about 5 minutes. A photograph of this heated film is indicated as slide 2 in FIG. 24. An SEM of this film is depicted in FIG. 26.

Figure 27:
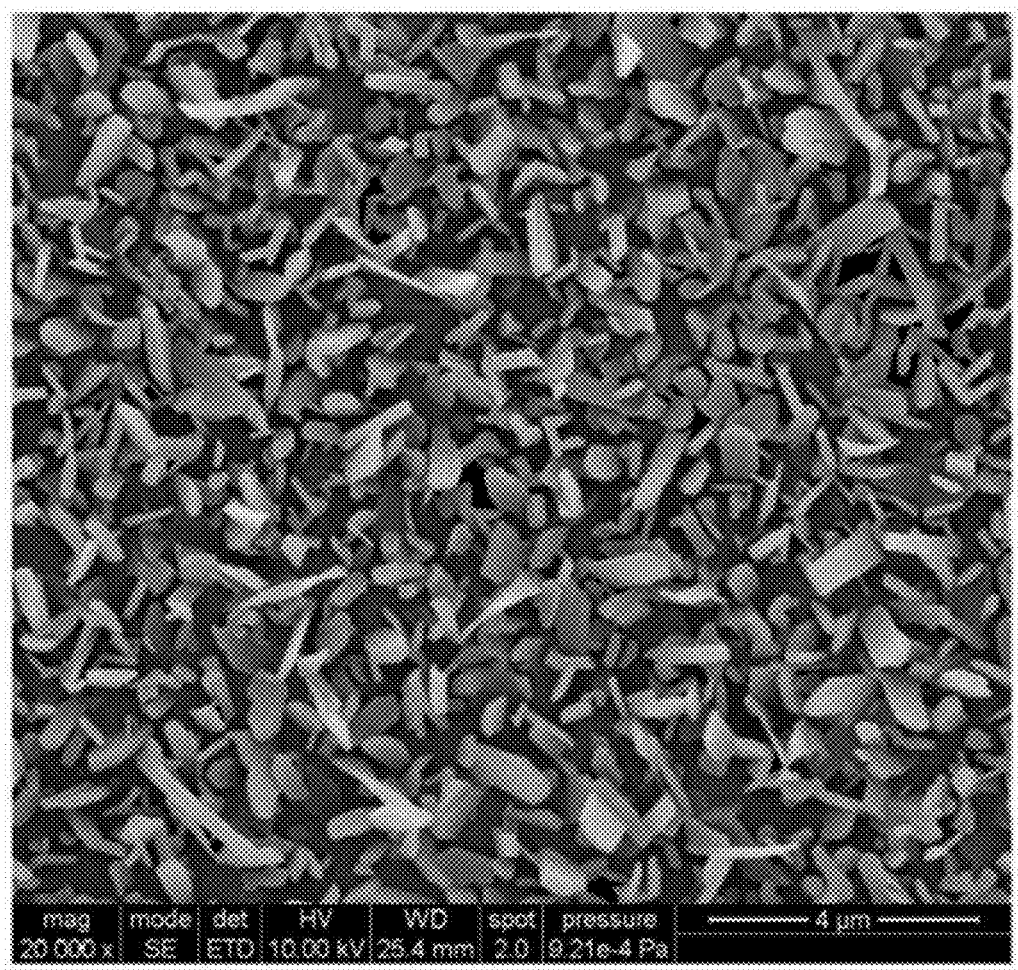
FIG. 27 depicts an SEM image of a surface of an embodiment of a porous film.

COMPOUND-8 was also deposited on a glass substrate and then heated at about 200° C. for about 30 minutes. A photograph of this heated film is indicated as slide 5 in FIG. 24. An SEM of this film is depicted in FIG. 27.

Figure 28:
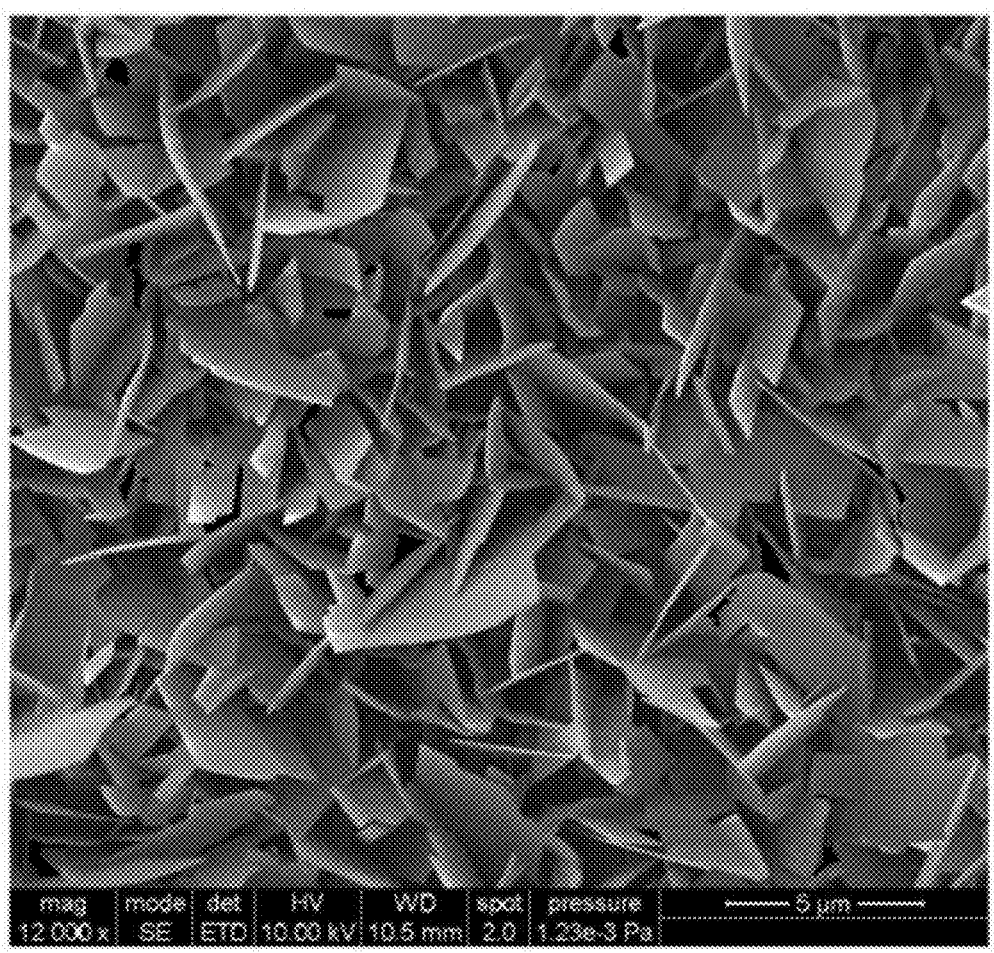
FIG. 28 depicts an SEM image of a surface of an embodiment of a porous film.

COMPOUND-8 was also deposited on a glass substrate and then heated at about 240° C. for about 5 minutes. A photograph of this heated film is indicated as slide 6 in FIG. 24. An SEM of this film is depicted in FIG. 28. COMPOUND-8 was also deposited on a glass substrate and then heated at about 300° C. for about 5 minutes. This appears to have caused a substantial amount of the film to evaporate. A photograph of this heated film is indicated as slide 7 in FIG. 24.

Figure 29:
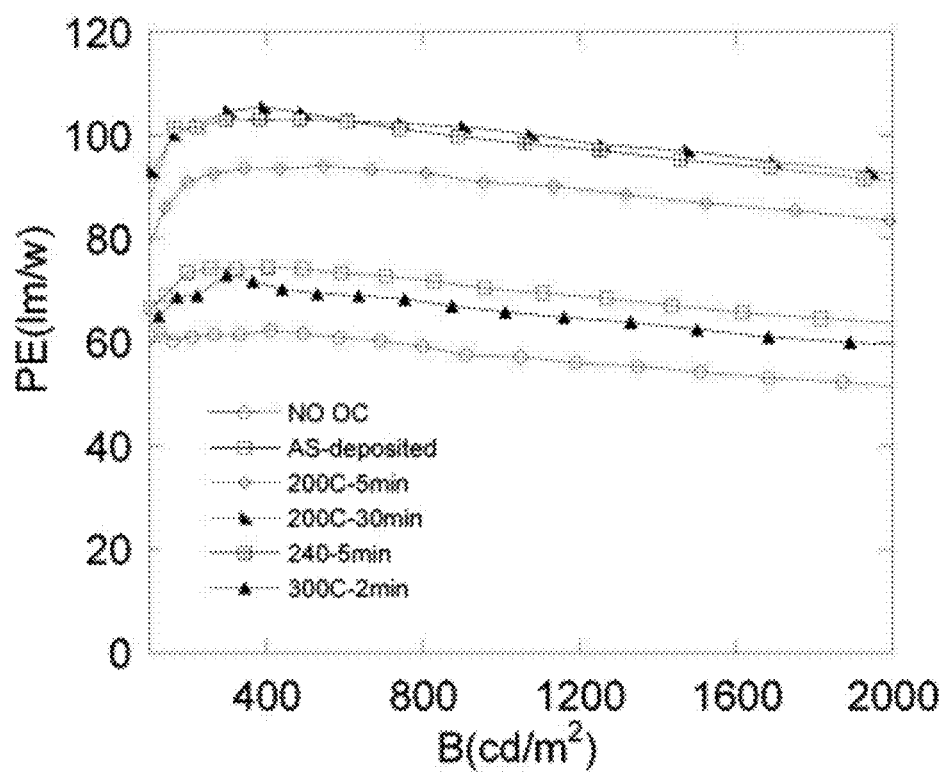
FIG. 29 is a plot of power efficiency as a function of luminance for some embodiments of devices described herein.

Films prepared as described above were coated onto the exterior surface of the transparent substrate of OLED A and the power efficiency was measured as a function of luminance, as shown in FIG. 29. The plot shows that deposition of COMPOUND-8 and heating at about 200 to about 240° C. for about 5 to about 30 minutes, or more, provides a film with a significant porous film effect such that the efficiency of the device is substantially improved. For example, heating the film at about 200° C. for about 30 minutes improved the power efficiency by about 1.82 times at about 2000 cd/m² luminance.

Device Example 4

Figure 30:
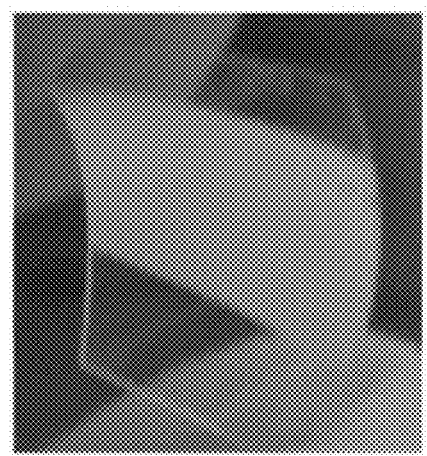
FIG. 30 is a photograph of an embodiment of the porous films described herein.

COMPOUND-3 was coated on a polyethylene terephthalate (PET) flexible substrate through vacuum deposition by the same method as the COMPOUND-3 layer on the Device D to form a layer having a thickness of about 6 um. The substrate with the coating was heated at 110° C. for 1 hour. FIG. 30 is a photograph of this coated flexible substrate.

Figure 31:
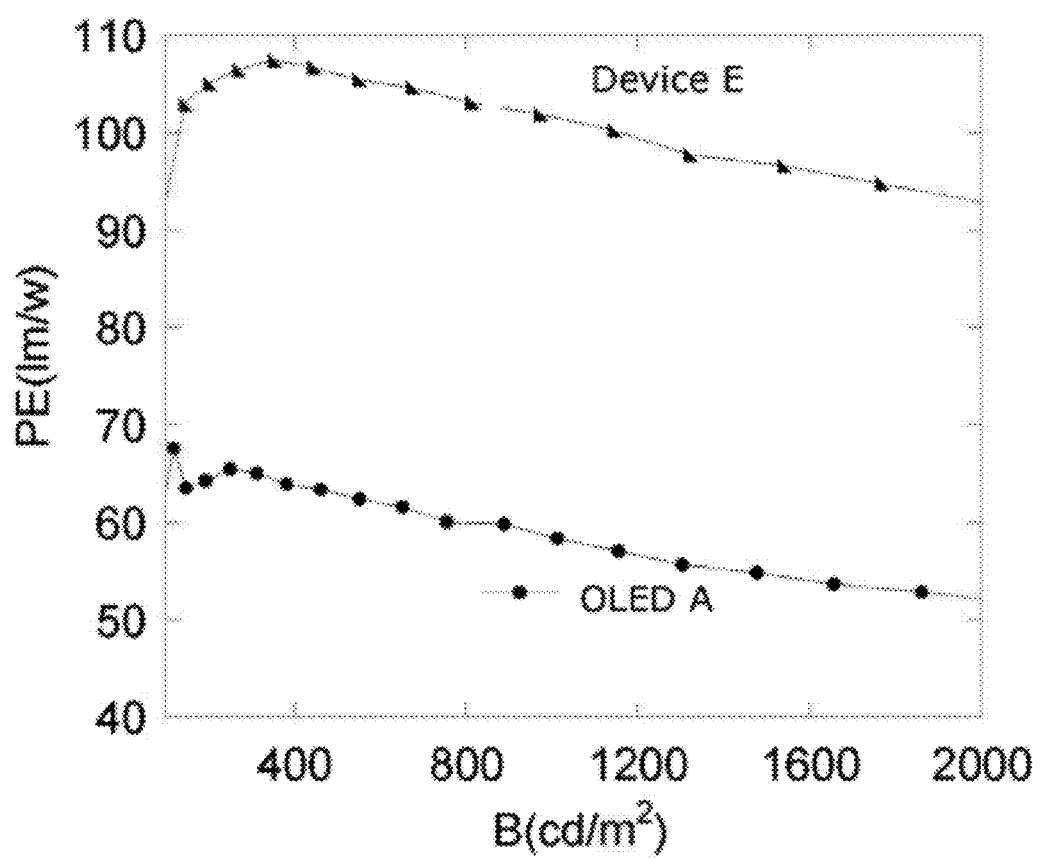
FIG. 31 is a plot of power efficiency as a function of luminance for some embodiments of devices described herein.

The coated flexible substrate was coupled to OLED A using the refractive index matching oil to obtain Device E. FIG. 31 is a plot of the power efficiency as a function of luminance of Device E as compared to OLED A. Device E, with the porous film, has significantly higher efficiency than OLED A without the porous film. For example, the power efficiency of Device E is 1.8 times greater than OLED A at 2000 cd/m².

Device Example 5

Device F

As described with respect to FIG. 7. The light-scattering layer (COMPOUND LAYER, 3 um thickness, 110° C. for 1 hour) was deposited on top of transparent substrate (glass). This light-scattering film was then coupled to the bottom of Device A using refractive index matching oil as a coupling medium to form Device F.

Device G

An encapsulation or protection layer was added to Device F as follows to provide Device G: an epoxy resin was applied around the edge of the light scattering layer, which upon curing built a gap between the transparent substrate and the encapsulation/protection layer that is another transparent cover glass.

Figure 32:
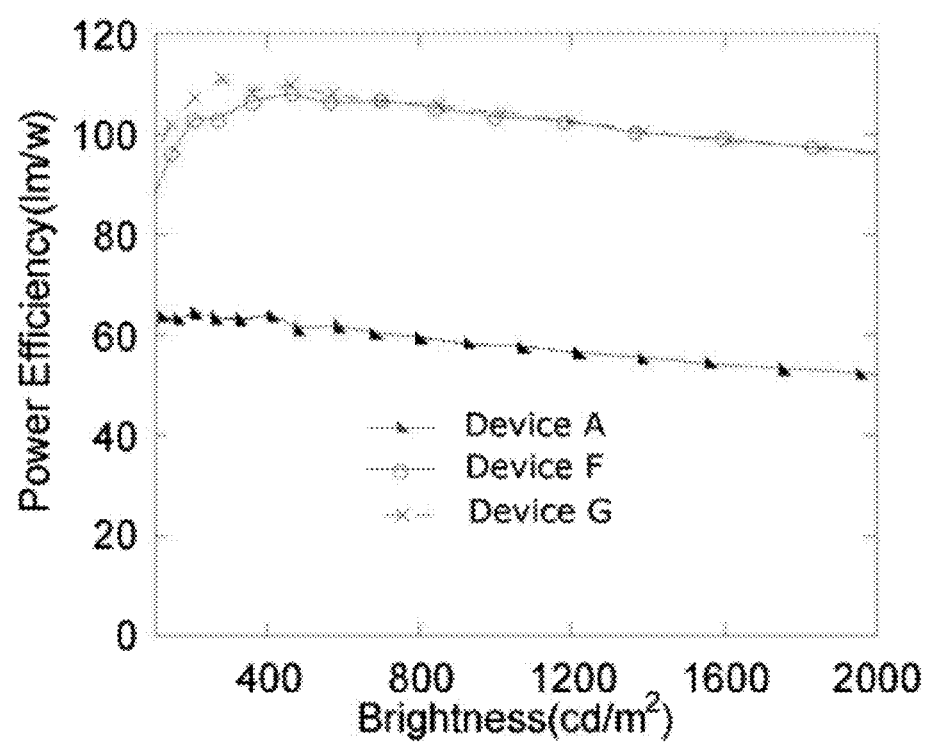
FIG. 32 is a plot of power efficiency as a function of luminance for some embodiments of devices described herein.

FIG. 32 is a plot of the power efficiency as a function of luminance for OLED A, Device F, and Device G. This plot shows that encapsulated device (Device G) shows similar light-outcoupling efficiency as the device (Device F) that is not encapsulated.

Although the claims have been described in the context of certain preferred embodiments and examples, it will be understood by those skilled in the art that the scope of the claims extend beyond the specifically disclosed embodiments to other alternative embodiments and/or uses and obvious modifications and equivalents thereof.

What is claimed is:

1. A compound represented by a Formula 2:

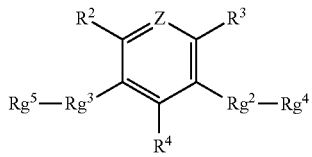

wherein Z is N;
$R^2$, $R^3$, and $R^4$ are independently H, $C_{1-6}$ alkyl, or —O—$C_{1-6}$ alkyl;
$Rg^3$, and $Rg^2$ are independently optionally substituted pyridinyl or phenyl; and
$Rg^5$ and $Rg^4$ are independently benzimidazol-2-yl, benzooxazol-2-yl, or benzothiazol-2-yl.

2. A compound represented by Formula 2:

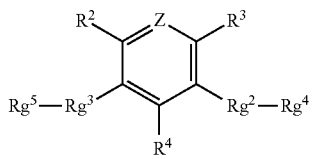

wherein Z is N or $CR^1$;

$R^1$ is H, $C_{1-6}$ alkyl, or phenyl optionally substituted with 1, 2, or 3 substituents selected from: $C_{1-6}$ alkyl and —O—$C_{1-6}$ alkyl;
$R^2$, $R^3$, and $R^4$ are independently H, $C_{1-6}$ alkyl, or —O—$C_{1-6}$ alkyl;
$Rg^2$ is optionally substituted pyridinyl;
$Rg^3$ is optionally substituted pyridinyl or phenyl; and
$Rg^5$ and $Rg^4$ are independently benzimidazol-2-yl, benzooxazol-2-yl, or benzothiazol-2-yl.

3. The compound of claim 2, wherein $R^1$, $R^2$, $R^3$, and $R^4$ are H.

4. The compound of claim 2, wherein $Rg^3$ is:

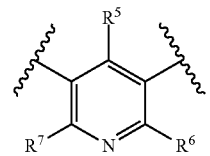

wherein $R^5$, $R^6$, and $R^7$ are independently selected from the group consisting of: H, $C_{1-6}$ alkyl, and —O—$C_{1-6}$ alkyl.

5. The compound of claim 4, wherein $R^5$, $R^6$, and $R^7$ are H.

6. The compound of claim 2, wherein $Rg^3$ is:

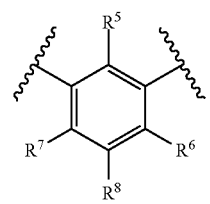

wherein $R^5$, $R^6$, $R^7$, and $R^8$ are independently selected from the group consisting of: H, $C_{1-6}$ alkyl, and —O—$C_{1-6}$ alkyl.

7. The compound of claim 6, wherein $R^5$, $R^6$, $R^7$, and $R^8$ are H.

8. The compound of claim 1, wherein $Rg^2$ and $Rg^3$ are independently:

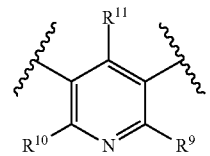

wherein $R^9$, $R^{10}$, and $R^{11}$ are independently selected from the group consisting of: H, $C_{1-6}$ alkyl, and —O—$C_{1-6}$ alkyl.

9. The compound of claim 8, wherein $R^9$, $R^{10}$, and $R^{11}$ are H.

10. The compound of claim 1, wherein $Rg^2$ and $Rg^3$ are independently:

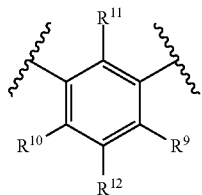

wherein $R^9$, $R^{10}$, $R^{11}$ and $R^{12}$ are independently selected from the group consisting of: H, $C_{1-6}$ alkyl, and —O—$C_{1-6}$ alkyl.

11. The compound of claim 10, wherein $R^9$, $R^{10}$, $R^{11}$, and $R^{12}$ are H.

12. The compound of claim 1, wherein $Rg^5$ is

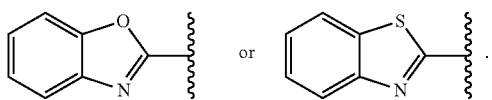 [SMILES: *c1nc2ccccc2o1 ; *c1nc2ccccc2s1]

13. The compound of claim 2, wherein $Rg^5$ is

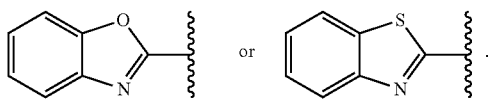 [SMILES: *c1nc2ccccc2o1 ; *c1nc2ccccc2s1]

14. The compound of claim 1, wherein $Rg^4$ is:

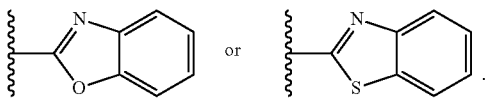 [SMILES: *c1nc2ccccc2o1 ; *c1nc2ccccc2s1]

15. The compound of claim 2, wherein $Rg^4$ is:

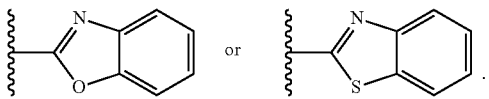 [SMILES: *c1nc2ccccc2o1 ; *c1nc2ccccc2s1]

16. The compound of claim 1, selected from the group consisting of:

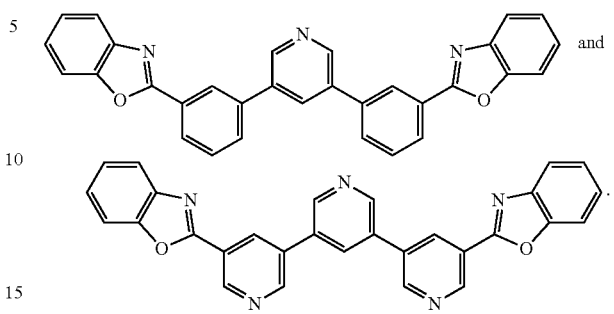

17. A light-emitting device comprising a compound according to claim 1 or 2.

18. The compound of claim 2, selected from the group consisting of:

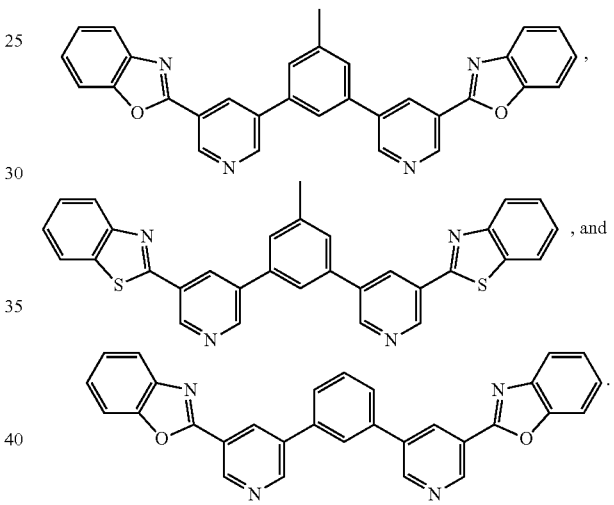

19. The compound of claim 2, wherein Z is $CR^1$; and $R^1$ is H or $C_{1-6}$ alkyl.

* * * * *